US009445716B2

(12) United States Patent
Liu et al.

(10) Patent No.: US 9,445,716 B2
(45) Date of Patent: Sep. 20, 2016

(54) OBTAINING DATA FOR AUTOMATIC GLAUCOMA SCREENING, AND SCREENING AND DIAGNOSTIC TECHNIQUES AND SYSTEMS USING THE DATA

(71) Applicants: Agency for Science, Technology and Research, Singapore (SG); Singapore Health Services Pte Ltd, Singapore (SG)

(72) Inventors: Jiang Liu, Singapore (SG); Zhuo Zhang, Singapore (SG); Wing Kee Damon Wong, Singapore (SG); Ngan Meng Tan, Singapore (SG); Fengshou Yin, Singapore (SG); Beng Hai Lee, Singapore (SG); Huiqi Li, Singapore (SG); Joo Hwee Lim, Singapore (SG); Carol Cheung, Singapore (SG); Tin Aung, Singapore (SG); Tien Yin Wong, Singapore (SG); Ziyang Liang, Singapore (SG); Jun Cheng, Singapore (SG); Baskaran Mani, Singapore (SG)

(73) Assignees: Agency for Science, Technology and Research, Singapore (SG); Singapore Health Services Pte Ltd, Singapore (SG)

( * ) Notice: Subject to any disclaimer, the term of this patent is extended or adjusted under 35 U.S.C. 154(b) by 0 days.

(21) Appl. No.: 14/828,262

(22) Filed: Aug. 17, 2015

(65) Prior Publication Data
US 2016/0100753 A1 Apr. 14, 2016

Related U.S. Application Data

(62) Division of application No. 13/510,290, filed as application No. PCT/SG2010/000434 on Nov. 16, 2010, now Pat. No. 9,107,617.

(30) Foreign Application Priority Data

Nov. 16, 2009 (SG) .................................. 200907651

(51) Int. Cl.
*A61B 3/00* (2006.01)
*G06T 7/40* (2006.01)
(Continued)

(52) U.S. Cl.
CPC ............... *A61B 3/0025* (2013.01); *A61B 3/12* (2013.01); *A61B 5/02007* (2013.01);
(Continued)

(58) Field of Classification Search
CPC ....... G06T 7/0012; G06T 7/40; G06T 7/401; G06T 7/402; G06T 7/407; G06T 2207/30041; G06T 2207/30168; G06K 9/0061; G06K 2209/05; A61B 3/0025; A61B 3/12; A61B 5/7221
See application file for complete search history.

(56) References Cited

U.S. PATENT DOCUMENTS 6,030,079 A 2/2000 Torii .............................. 351/205
6,053,865 A 4/2000 Sugiyama et al. ............ 600/300
(Continued)

FOREIGN PATENT DOCUMENTS

AU 2008241867 A 10/2008
JP 2007181537 A 7/2007
(Continued)

OTHER PUBLICATIONS

J. Liu, et al., "ARGALI: An Automatic Cup-to-Disc Ratio Measurement System for Glaucoma Analysis Using Level-Set Image Processing", 13th International Conference on Biomedical Engineering (ICBME2008), 4 pgs., (Dec. 2008).
(Continued)

*Primary Examiner* — Andrew W Johns
(74) *Attorney, Agent, or Firm* — Blakely, Sokoloff, Taylor & Zafman LLP

(57) ABSTRACT

A non-stereo fundus image is used to obtain a plurality of glaucoma indicators. Additionally, genome data for the subject is used to obtain genetic marker data relating to one or more genes and/or SNPs associated with glaucoma. The glaucoma indicators and genetic marker data are input into an adaptive model operative to generate an output indicative of a risk of glaucoma in the subject. In combination, the genetic indicators and genome data are more informative about the risk of glaucoma than either of the two in isolation. The adaptive model may be a two-stage model, having a first stage in which individual genetic indicators are combined with respective portions of the genome data by first adaptive model modules to form respective first outputs, and a second stage in which the first outputs are combined by a second adaptive mode. Texture analysis is performed on the fundus images to classify them based on their quality, and only images which are determined to meet a quality criterion are subjected to an analysis to determine if they exhibit glaucoma indicators. Also, the images are put into a standard format. The system may include estimating the position of the optic cup by combining results from multiple optic cup segmentation techniques. The system may include estimating the position of the optic disc by applying edge detection to the funds image, excluding edge points that are unlikely to be optic disc boundary points, and estimating the position of an optic disc by fitting an ellipse to the remaining edge points.

7 Claims, 21 Drawing Sheets

(51) Int. Cl.
A61B 3/12 (2006.01)
A61B 5/02 (2006.01)
A61B 5/00 (2006.01)

(52) U.S. Cl.
CPC .......... *A61B 5/7264* (2013.01); *A61B 5/7267* (2013.01); *A61B 5/7275* (2013.01); *G06T 7/40* (2013.01); *G06T 2207/30041* (2013.01)

(56) References Cited

U.S. PATENT DOCUMENTS

2005/0251013 A1* 11/2005 Krishnan et al. ............. 600/407
2007/0109499 A1 5/2007 Yan et al. ..................... 351/221

FOREIGN PATENT DOCUMENTS

| WO | WO 2008/152656 A2 | 12/2008 |
|----|-------------------|---------|
| WO | WO 2009/126112 A1 | 10/2009 |
| WO | WO 2009/139722 A1 | 11/2009 |
| WO | WO 2010/044459 A1 | 4/2010 |
| WO | WO 2010/071597 A1 | 6/2010 |

OTHER PUBLICATIONS

Jiang Liu, et al., "Detection of Pathological Myopia by Pamela with Texture-Based Features through an SVM Approach", Journal of Healthcare Engineering, vol. 1, No. 1, 7 pgs., (Mar. 2010).

PCT International Search Report for PCT Counterpart Application No. PCT/SG2010/000434 containing Communication relating to the Results of the International Search Report, 6 pgs., (Mar. 9, 2011).

PCT Written Opinion of the International Searching Authority for PCT Counterpart Application No. PCT/SG2010/000434, 9 pgs., (Mar. 9, 2011).

PCT Notification concerning Transmittal of International Preliminary Report on Patentability (Chapter I of the Patent Cooperation Treaty) for PCT Counterpart Application No. PCT/SG2010/000434, 11 pgs., (May 31, 2012).

Michael D. Abramoff, et al., "Automated Segmentation of the Optic Disc from Stereo Color Photographs using Physiologically Plausible Features", Investigative Ophthalmology & Visual Science, vol. 48, No. 4, pp. 1665-1673, (Apr. 2007).

Naoto Inoue, et al., "Development of a Simple Diagnostic Method for the Glaucoma using Ocular Fundus Pictures", Proceedings of the 2005 IEEE Engineering in Medicine and Biology 27th Annual Conference, pp. 3355-3358, (Sep. 1-4, 2005).

J. Liu, et al., "Optic Cup and Disk Extraction from Retinal Fundus Images for Determination of Cup-to-Disc Ratio", Conf. Proc. IEEE ICIEA, pp. 1828-1832, (2008).

Wishal D. Ramdas, et al., "A Genome-Wide Association Study of Optic Disc Parameters", PLoS Genetics, vol. 6, No. 6, e1000978, pp. 1-12, (Jun. 2010).

D.W.K. Wong, et al., "Automated Detection of Kinks from Blood Vessels for Optic Cup Segmentation in Retinal Images", Proc. of SPIE Medical Imaging, vol. 7260, 8 pgs., (Feb. 2009).

Juan Xu, et al., "Optic Disk feature Extraction via Modified Deformable Model Technique for Glaucoma Analysis", Pattern Recognition, vol. 40, pp. 2063-2076, (2006).

Zhuo Zhang, et al., "ORIGA-light: An Online Retinal Fundus Image Database for Glaucoma Analysis and Research", 32nd Annual International Conference of the IEEE EMBS, pp. 3065-3068, (Aug. 31-Sep. 4, 2010).

Zhuo Zhang, et al., "Optic Disc Region of Interest Localization in Fundus Image for Glaucoma Detection in ARGALI", Proc. of the 5th International Conference on Industrial Electronics & Applications, pp. 1686-1689, (2010).

Xiaolu Zhu, et al., "Detection of the Optic Disc in Images of the Retina using the Hough Transform", 30th Annual International IEEE EMBS Conference, pp. 3546-3549, (Aug. 20-24, 2008).

* cited by examiner

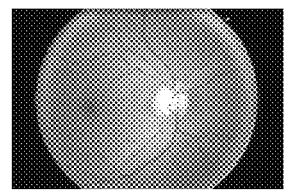 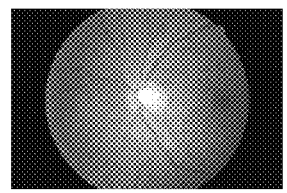
Fig. 9(a)　　　　　　　Fig. 9(b)
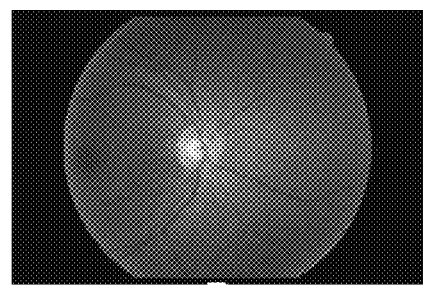 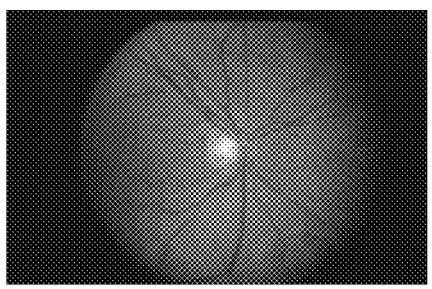
Fig. 9(c)　　　　　　　Fig. 9(d)
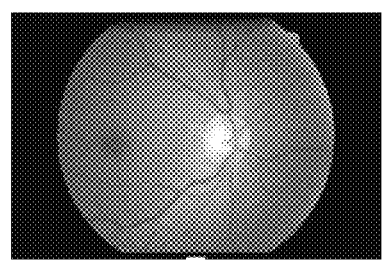 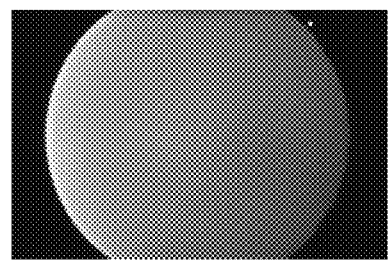
Fig. 10(a)　　　　　　　Fig. 10(b)

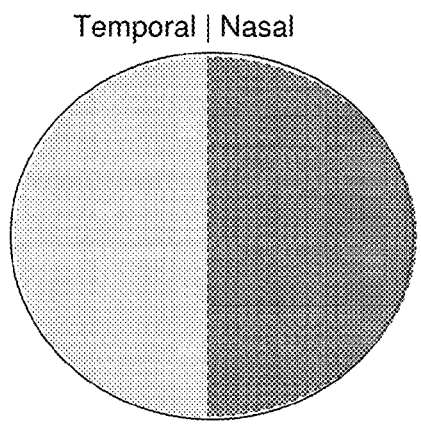
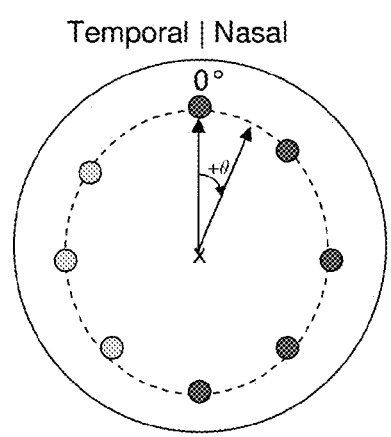
Fig. 14(a)                    Fig. 14(b)
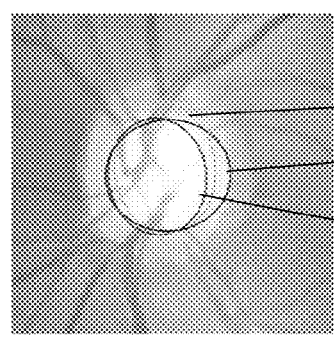
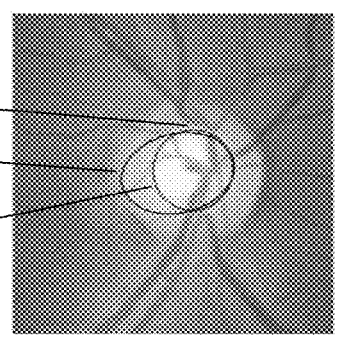
Fig. 15 (a)                   Fig. 15 (b)

OBTAINING DATA FOR AUTOMATIC GLAUCOMA SCREENING, AND SCREENING AND DIAGNOSTIC TECHNIQUES AND SYSTEMS USING THE DATA

CROSS-REFERENCE TO RELATED APPLICATIONS

This patent application is a divisional of U.S. patent application Ser. No. 13/510,290, filed May 16, 2012, now U.S. Pat. No. 9,107,617, issuing on Aug. 18, 2015, which is a U.S. National Phase Application under 35 U.S.C. §371 of International Application No. PCT/SG2010/000434, filed Nov. 16, 2010, entitled OBTAINING DATA FOR AUTOMATIC GLAUCOMA SCREENING, AND SCREENING AND DIAGNOSTIC TECHNIQUES AND SYSTEMS USING THE DATA, which claims priority to Singapore Patent Application No. 200907651-4, filed Nov. 16, 2009.

FIELD OF THE INVENTION

The present invention relates to methods and systems for obtaining data useful in detecting glaucoma in a human subject. It further relates to methods and systems for generating an output indicative of a high likelihood of glaucoma. The output may be used in screening subjects for glaucoma, or even performing a glaucoma diagnosis for a subject.

BACKGROUND OF THE INVENTION

Glaucoma is a chronic eye condition in which the nerve that connects the eye to the brain (optic nerve) is progressively damaged. Patients with early glaucoma do not have visual symptoms. Progression of the disease results in loss of peripheral vision, so patients may complain of "tunnel vision" (only being able to see the centre). Advanced glaucoma is associated with total blindness. Worldwide, it is the second leading cause of blindness, affecting 60 million people by 2010, and responsible for approximately 5.2 million cases of blindness (15% of the total burden of world blindness). The problem is even more significant in Asia, as Asians account for approximately half of the world's glaucoma cases. Finally, because it is a condition of aging, it will affect more people in Singapore and Asia as their population ages.

Recent years' development in the understanding of the genetics of glaucoma allows for the first time a molecular insight into the pathogenesis glaucoma. Ophthalmologists have long recognized the presence of a subgroup of glaucoma that follows a mendelian form of inheritance (recessive or dominant). With large enough families, linkage analysis is a very powerful technique that can quickly identify the culprit genes in these families. Moreover, even the more common forms of glaucoma which do not typically follow a clear mendelian pattern of inheritance, are known to cluster in families. This indicates the existence of "genetic predisposition" that may differ between various populations.

Two genes (MYOC and OPTN) have been shown to account for a small fraction of open-angle glaucoma cases. Moreover, the CYP1B1 gene has been found to be responsible for more than half of cases of congenital glaucoma in some populations studied. Many more regions around the genome have been identified as genetic risk factors for glaucoma but the actual genes involved have not been found. Future studies are expected to examine the roles of more glaucoma genes in populations.

Genome wide association studies (GWAS) look for associations between DNA sequence variants and phenotypes of interest. They do so by studying hundreds of thousands of individuals with different phenotypes, and determining their genotype at the positions of hundreds of thousands of single DNA mutations (single-nucleotide polymorphisms, SNPs). About 600 human GWASs have examined 150 diseases and traits, and found 800 SNP associations. They are useful in finding the molecular pathways of disease, but usually not useful in finding genes that predict risks of disease.

These studies normally compare the DNA of two groups of participants: people with the disease (cases) and similar people without (controls). Each person gives a sample of cells and DNA is extracted from these cells, and spread on gene chips, which can read millions of DNA sequences. These chips are read into computers, where they can be analyzed with bioinformatic techniques. Rather than reading the entire DNA sequence, these systems usually read SNPs that are markers for groups of DNA variations (haplotypes).

If genetic variations are more frequent in people with the disease, the variations are said to be associated with the disease. The associated genetic variations are then considered as pointers to the region of the human genome where the disease-causing problem is likely to reside.

Currently, new techniques of GWAS have not only successfully identified known SNPs that are associated with diseases such as Parkinson, AMD, diabetes and etc, they have also identified suspected SNPs that are associated with the disease.

Recently, researchers from Netherlands conducted a large-scale GWA study [1] on retinal optic disc parameters, including optic disc and vertical cup-disc ratio, both are highly heritable but genetically largely undetermined. The study analyzed datasets from several European population studies, found several genome-wide significant loci for optic disc area and vCDR respectively, and identified three susceptible loci that are associated with open-angle glaucoma.

Glaucoma cannot presently be cured, but treatment can prevent progression of the disease, so early detection is critical to prevent blindness. However, routine screening for glaucoma in the whole population is not cost effective and limited by poor sensitivity of current tests. However, screening may be useful for high risk individuals, such as first degree relatives of a glaucoma patient, older age (e.g., 65 years and older) and elderly Chinese women (who are at risk of angle closure glaucoma). So far no technique employing genetic information has been employed in screening patients or assessing risk factors, and indeed it may not be possible to extract sufficient information from genetic data alone to make a screening operation possible.

Furthermore, currently, there is no systematic way to detect and manage early glaucoma. Glaucoma patients are often unaware they have the condition, and visit ophthalmologist (eye doctors) only when severe visual loss is already present. Treatment at this stage is limited to surgery, is expensive, requires skilled personnel, and does not restore vision.

There are three current methods to detect glaucoma:
(1) Assessment of raised intraocular pressure (IOP),
(2) Assessment of abnormal visual field
(3) Assessment of damaged optic nerve IOP measurement is neither specific nor sensitive enough to be an effective screening tool. Visual field testing requires special equipment only present in tertiary hospitals.

As for assessing damage to the optic nerve, FIGS. 1(a) and 1(b) show different structures of the optic disc (the location where the ganglion cell axons exit the eye to form the optic nerve) respectively in the case of a normal optic disc and a glaucomatous disc. The upper part of the FIGS. 1(a) and 1(b) is a cross-sectional view, while the lower part of the figures is a perspective view. Among other physiological features, the glaucomatous disc has a wider optic cup. Assessment of damaged optic nerves is more promising and superior to IOP or visual field testing, but requires a trained specialist (ophthalmologist), or specialized equipment such as the HRT (Heidelberg Retinal Tomography). Furthermore, optic disc assessment by an ophthalmologist is subjective and the availability of HRT is very limited because of the cost involved as well as a shortage of trained operators.

ARGALI [2] (an Automatic cup-to-disc Ratio measurement system for Glaucoma AnaLlysls), a cup-to-disc ratio is derived from a single, non-stereo fundus image, and used to automatically measure the optic nerve. The ARGALI system makes use of contour-based methods in the determination of the cup and disc, through analysis of pixel gradient intensity values throughout the retinal image. In some cases, where the gradient values are gradual, difficulties in the correct cup identification can occur.

In [3] obtains a cup contour based on color space analysis of a non-stereo fundus image, based on pixel color. This technique has the weakness that the color information may not be accurate.

In [4], analysis of blood vessel architecture was used to determine the location of the cup within the optic disc. Using this method, bends in the retinal vasculature over the cup/disc boundary, also known as kinks, were used to determine the physical location of the optic cup. Although this method is non-reliant on color or pallor, some of the challenges include correct identification of kinks, as well as the absence of kinks in some retinal images.

In [5], discriminatory color-based analysis was used to determine the location of the cup and disc from retinal images. Histogram color analysis was performed on the image to determine the threshold cutoff between the cup and the disc. To determine the disc, statistical analysis of the pixel intensities was performed on the retinal image different features. However, no results were presented on the accuracy of results compared to clinical ground truth.

Some other work has also been presented [6, 7] making use of information from stereo photographs for the determination of the optic cup and disc. While some of the results presented are promising, the key challenge lies in the use of stereoscopic photography as compared to monocular ("non-stereo") photography. Stereoscopic photography demands specific hardware and requires specialized training, both of which may be unsuitable for the needs for mass screening.

SUMMARY OF THE INVENTION

The present invention aims, in some aspects, to provide new and useful methods and systems for using images to extract data useful for detecting glaucoma from fundus images (e.g. a single fundus image per eye).

Furthermore, in some aspects, the present invention proposes techniques for generating an output indicating a high likelihood of glaucoma in a patient. This output can be used in a screening procedure, or even as part of an eventual diagnosis of glaucoma.

A first aspect of the invention proposes in general terms that a non-stereo fundus image (retinal image) is analysed to obtain a plurality of glaucoma indicators. Additionally, genome data (genetic data) for the patient is used to obtain genetic marker data relating to one or more genes and/or SNPs associated with glaucoma. The glaucoma indicators and genetic marker data are input into an adaptive model operative to generate an output indicative of a risk of glaucoma in the subject. In combination, the genetic indicators and genome data are more informative about the risk of glaucoma than either of the two in isolation.

The adaptive model may be a two-stage model incorporating a first stage in which individual genetic indicators are combined with respective portions of the genome data by first adaptive model modules to form respective first outputs, and a second stage in which the first outputs are combined by a second adaptive model.

The three following aspects of the invention relate to features which may be employed in a system according to the first aspect of the invention, but which may alternatively be employed in one of the prior art techniques described above.

A second aspect of the invention proposes that texture analysis is performed on the fundus images to classify them based on their quality, and that only images which are determined to meet a quality criterion are subjected to an analysis to determine if they exhibit glaucoma indicators.

Preferably, there is additionally a process of converting received fundus images taken with different camera settings to a standard format. Since the fundus cameras are complex in design and difficult to manufacture to clinical standards, only a few manufacturers exist (Topcon, Zeiss, Canon, Nidek and Kowa). However, there are various models for each brand and each model may have a few different settings. This can lead to great difficulty for an automated system to analyze and grade images taken by different cameras. By standardizing these images before processing to extract glaucoma markers, this aspect of the invention extends the coverage to a wider variety of camera.

The step of pre-processing the fundus images preferably further includes generating control parameters to be used in controlling (including initializing) algorithms to identify structural glaucoma indicators.

A third aspect of the invention proposes that an optic cup segmentation technique uses a plurality of techniques for obtain respective estimates of the position of an optic cup in an image. These estimates are combined by a fusion algorithm to produce data indicating an improved estimate of the position of the optic cup. The fusion algorithm depends upon an angular position about an estimated centre of the optic cup. This improved estimate of the position of the optic cup may, for example, be employed in a system according to the first aspect of the invention, or alternatively to enhance some of the prior art techniques discussed above (such as ARGALI) which involve estimation of the position of the optic cup.

A fourth aspect of the invention proposes that an optic disc estimation includes an edge detection step applied to a non-stereo retinal image, a step of excluding edge points that are unlikely to be optic disc boundary points, and a step of estimating the position of an optic disc by fitting an ellipse to the remaining edge points.

BRIEF DESCRIPTION OF THE DRAWINGS

Embodiments of the invention will now be described for the sake of example only with reference to the following drawings, in which:

FIGS. 9(a), 9(b), 9(c), and 9(d) show the format of images from four different databases which may be used by the embodiment of FIG. 2;

FIGS. 10(a) and 10(b) respectively show images of high and low quality, as classified by the structure of FIG. 7;

FIG. 14(a) illustrates a first model used by the SHE module of FIG. 12;

FIG. 14(b) illustrates a second model;

FIGS. 15(a) and 15(b) illustrate two examples of results from the SHE module of FIG. 12;

DETAILED DESCRIPTION OF THE EMBODIMENTS

Section 1 of the following text describes an embodiment of the invention ("AGLAIA"). In section 2 it describes four optional features of the embodiment, the first three of which have application to other systems for studying fundus images.

1. The Embodiment

Figure 1A:
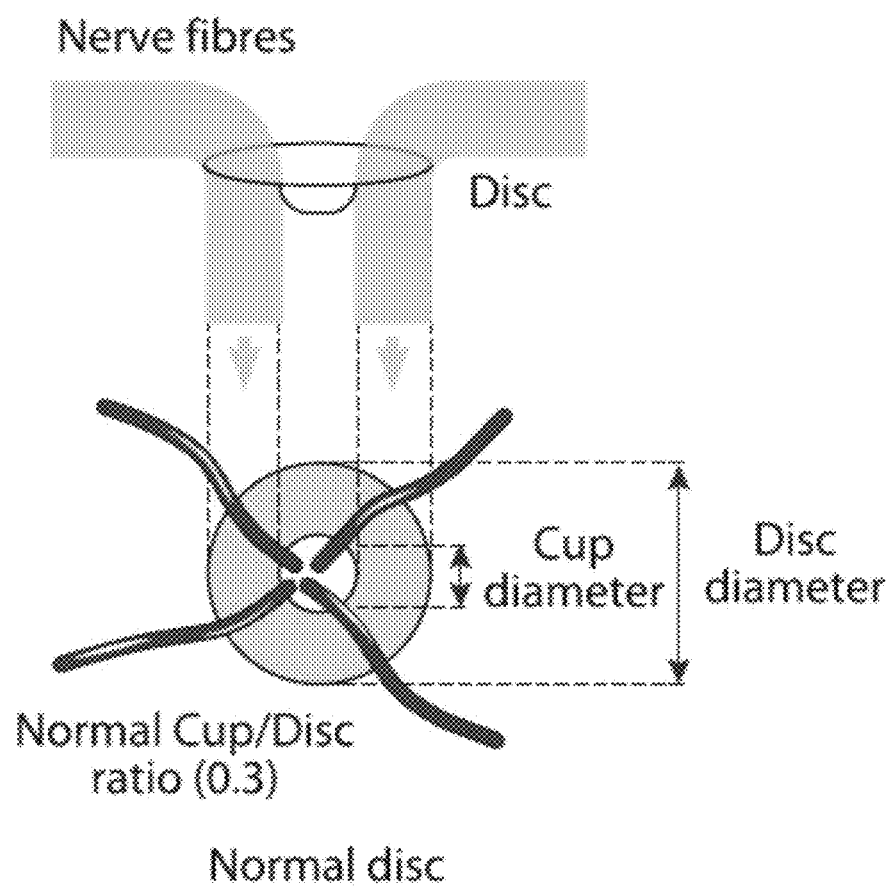
FIG. 1, which is composed of FIGS. 1(a) and 1(b), illustrates the different structures of normal optic discs and glaucomatous discs.
Figure 1B:
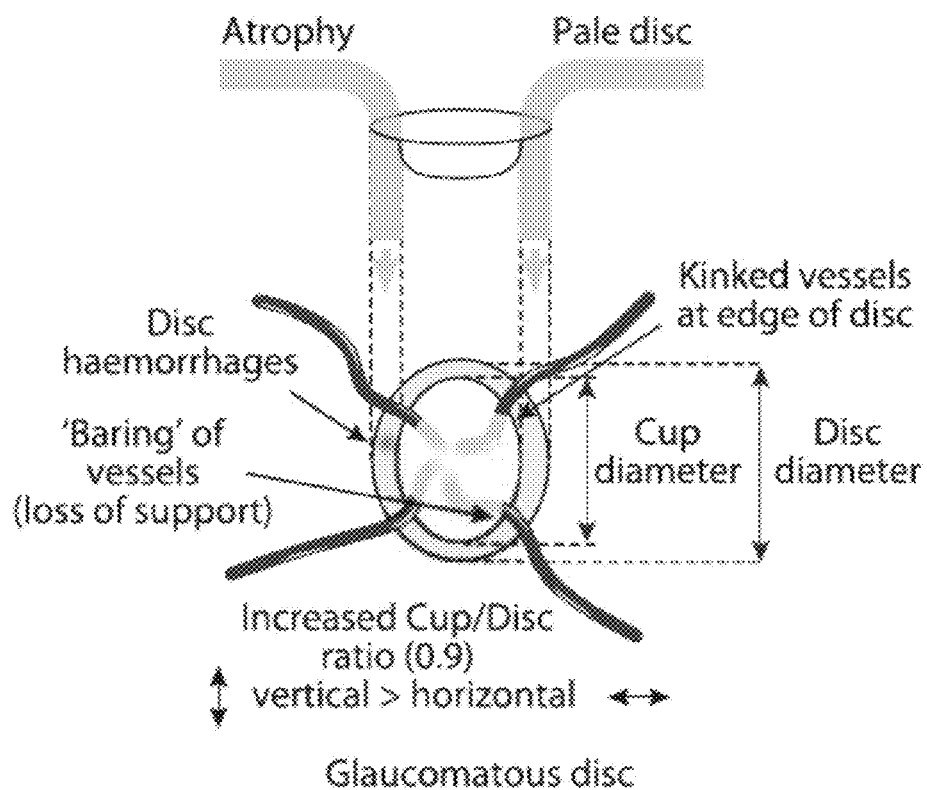
Figure 2:
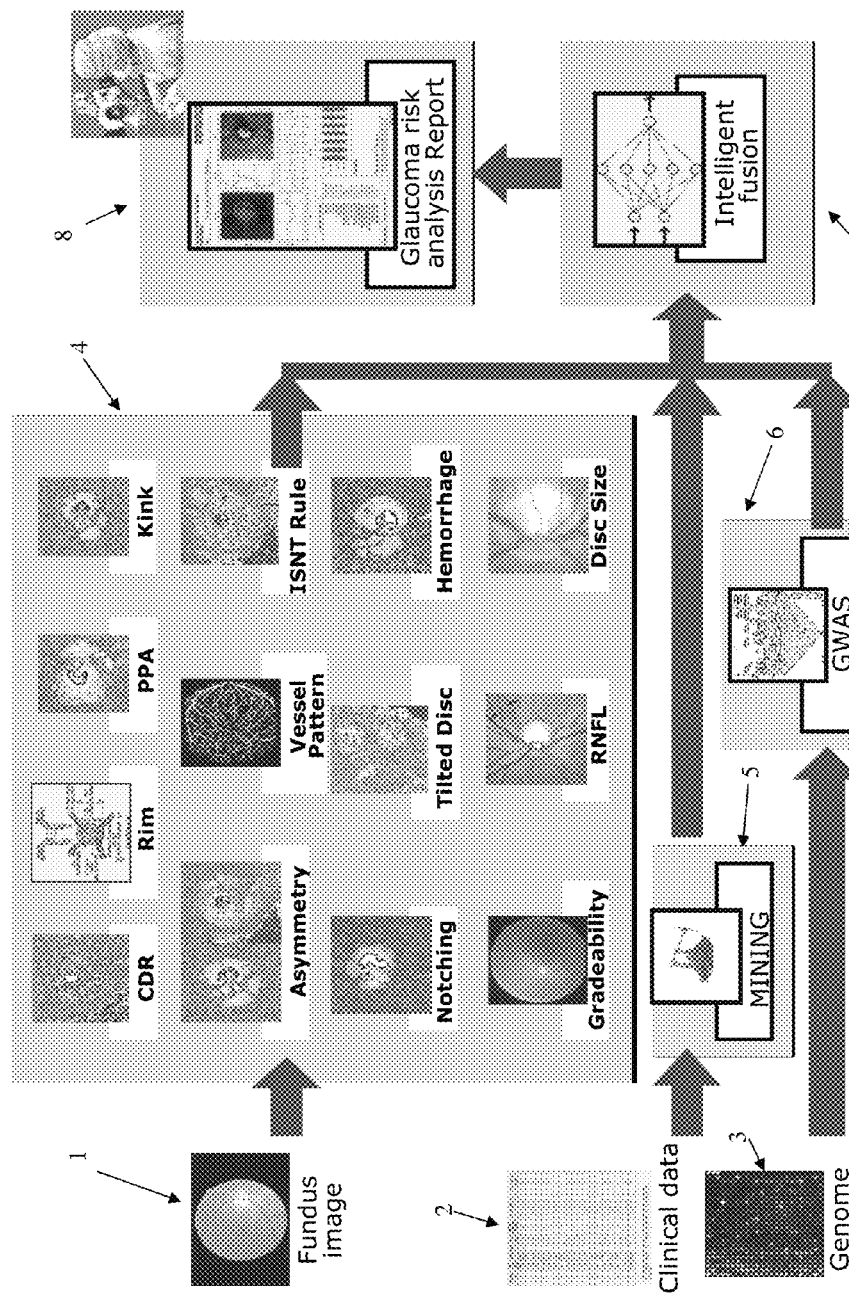
FIG. 2 shows the structure of an embodiment of the invention.

The structure of an embodiment of the invention is illustrated schematically in FIG. 2. The embodiment is referred to as "AGLAIA" (Architecture for automatic glaucoma diagnosis and its genetic association study through medical image informatics). There are three inputs to the system. A first input is at least one (typically, exactly one) non-stereo fundus image 1 of each eye of a subject. A second input is clinical data 2 describing the medical history of the subject. The third input is genome data 3 (genetic data), for example data obtained from a DNA microarray. The DNA microarray typically measures the respective levels of expression in the subject of each of a large number of genes, or detects single nucleotide polymorphisms (SNPs).

The fundus image 1 is input to a unit 4 which identifies a plurality of features (e.g. by extracting numerical parameters) which are indicative of early glaucoma damage. As described in more detail below, these features may comprise one or more of the following 13 features:

Cup-to-disc ratio (CDR)

Disc hemorrhage (DH)

Thinning of the NRR (NeuroRetinal Rim, which means the part of the optic disc which is outside the optic cup)

Compliance of NRR width by the 'ISNT Rule'

Inter-eye asymmetry

Parapapillary atrophy (PPA)

Notching of the NRR

Blood vessel pattern analysis

Blood vessel kink analysis

Tilted Disc—quantify the degree of tilting based on the disc contour

Disc Size—automatically classify disc size to "large, medium or small" categories based on automatic disc measurement Gradeability—analyze the image and determine gradeability Check the presence of RNFL (Retinal Nerve Fiber Layer) defect.

Of these, the most valuable features are, in order of decreasing importance, the identification of the CDR, the kink analysis and the hemorrhages, so preferably these are included.

We now describe the 13 respective modules of the unit 4 which assess each of these features. Information may flow from one of these modules to another. For example, as described below the module for estimating the cup-to-disc ratio (CDR) performs an algorithms which includes estimating the positions of the optic disc and optic cup within each fundus image 1 (referred to as "segmenting" the optic disc and the optic cup), and the results are used by other of the modules.

1. Cup-to-Disc Ratio (CDR)

Optic disc cupping is one of the most important features in the diagnosis of glaucoma. The module of the unit 4 which obtains the CDR may employ the AGRALI method described in [2]. The optic disc is obtained by a variational level-set approach, which is based on global optimization concepts, and is used to segment the disc boundary and extract the optic disc region from the retinal image. Segmentation of the optic cup is more challenging than the optic disc due to the optic cup's interweavement with blood vessel and surrounding tissues. A color histogram analysis of the image is first carried out, and is subsequently followed by the application of level-set algorithms to segment the cup boundary. The segmented cup is then smoothened in two separate instances, one making use of ellipse fitting and another in which a maximum inscribed fitted circle is used. Finally, a neural network is trained to fuse the cup-to-disc calculation results from the level-set algorithms and the results after different smoothing processes. This neural network learning mechanism integrates the knowledge embedded in the clinical practice and provides an optimal CDR for the glaucoma screening, diagnosis and analysis.

Note that in section 2.2 below, we describe an optional "spatial heuristic ensembling" module which may included in the embodiment to obtain an even more accurate estimate of the position of the optic cup. Furthermore, in section 2.3 below, we describe an enhanced method for detecting the optic disk. When these optional features are implemented, the improved estimates can be used in several ways, one of which is to input one or each of them into the neural network of this module instead of inputting the corresponding objects obtained using the method of [2].

2. Disc Haemorrhage

A disc haemorrhage (DH) is a clinical sign which is often associated with glaucomatous optic nerve damage. Medical image processing technology is used to detect any disc haemorrhage. Rarely found in normal eyes, disc haemorrhages are detected in about 4% to 7% of eyes with glaucoma. These are usually dot-shaped when within the NRR and flame-shaped (splinters) when on, or adjacent to, the disc margin. Flame-shaped haemorrhages within the RNFL (retinal nerve fiber layer) that cross the scleral ring in the absence of disc edema (i.e. Drance haemorrhages), are highly suggestive of progressive optic nerve damage. DHs are more common in the early stages of glaucoma. They are usually located in the infero- or supero-temporal disc regions and are more frequent in normal tension glaucoma. Depending on their original size, they are visible for about 1 to 12 weeks after the initial bleed. A localized RNFL defect and/or neuroretinal rim (NRR) notch may be detected, corresponding to a visual field defect.

The embodiment detects DHs by first identifying a ring-shaped region of interest (ROI) encompassing the optic disc boundary. Two dilated images (produced by morphological dilation) are then generated. The first dilated image is formed by applying edge detection methods on the green and grey channels of the fundus image to detect and remove the retinal blood vessels. Edge detection is then applied on the red channel of the retinal fundus image to obtain an outline of an optic disc region to construct the second dilated image. The two dilated images are then fitted (overlaid pixel by pixel) together to create a new summed image. The identified region of interest (ROI) is then masked on the summed image to extract blood vessels. Colour-based analysis (e.g. wavelet-based, model-based, thresholding-based analysis etc) is performed to detect disc haemorrhages from the extracted blood vessels regions in the identified region of interest to pinpoint the candidate disc haemorrhages. Lastly, knowledge-based constraints (including both clinical and image property based constraints) are applied in post-processing to screen and identify the true disc haemorrhages.

3. Thinning of Neuroretinal Rim (NRR)

Figure 3:
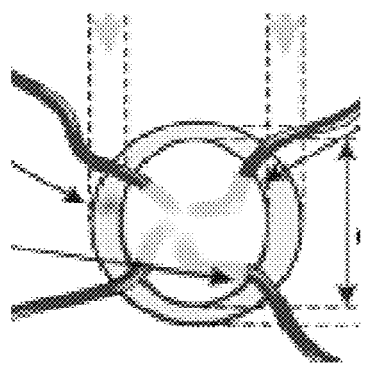
FIG. 3 illustrates thinning of the neuroretinal rim in a glaucomatous disc, which is detected in the embodiment of FIG. 2.

Neuroretinal rim loss is preferentially located at the inferotemporal and supertemporal in early glaucoma. Therefore, assessment of neuroretinal rim (NRR) thinning is very important for the detection of glaucoma. The measurement of the neuroretinal rim loss would also complement the Parapapillary atrophy (PPA) detection, as the site of the largest area of atrophy tends to correspond with the part of the disc with most NRR loss. An example of thinning of NRR at superior and inferior regions is shown in FIG. 3. The algorithm uses the optic cup and optic disc produced by the CDR module. The NRR will be measured around the optic disc, and can include measuring widths as well as areas in the superior, inferior, nasal and temporal regions, as well as combinations of these regions.

4. Compliance of NRR Width by 'ISNT Rule'

Figure 4B:
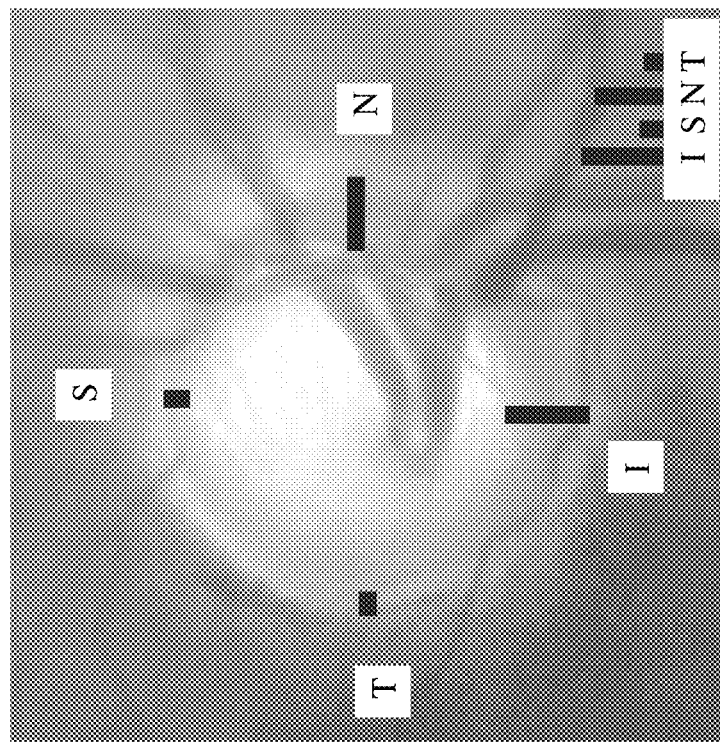
FIG. 4, which is composed of FIGS. 4(a) and 4(b), illustrates how a normal optic disc obeys the ISNT rule, and how a glaucomatous disc does not, as detected by the embodiment of FIG. 2.
Figure 4A:
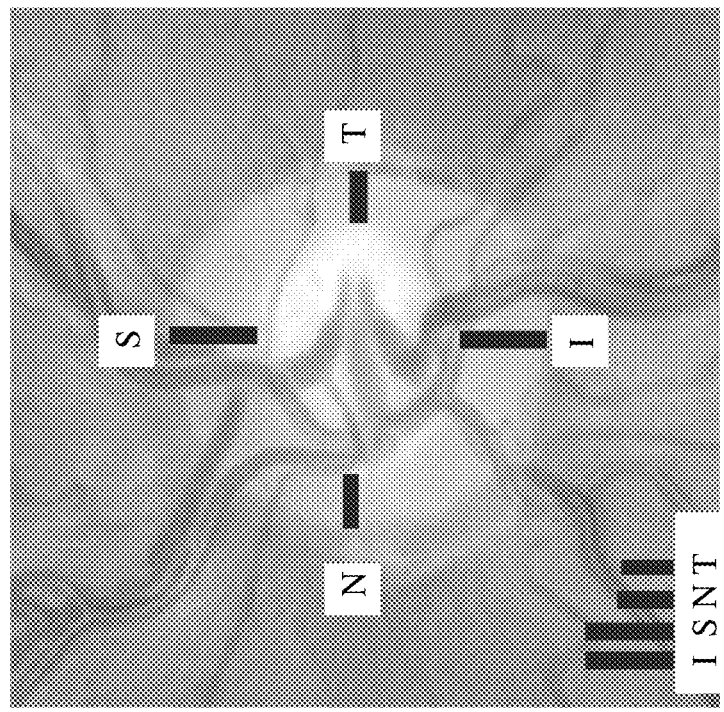

The neuroretinal rim (NRR) is usually broadest inferiorly, followed by superiorly, then nasally, and finally temporally. This is illustrated in FIG. 4(a), in which the widths of the NRR in each direction are shown. This is referred to as the Jonas 'ISN'T' rule. In large optic discs, the 'ISNT' rule is less apparent, with the NRR appearing to have equal thickness all around the disc. In glaucoma, NRR loss can be diffuse, in all sectors of the optic disc, or localized, forming a "notch", and the ISNT rule is not adhered to, as shown in FIG. 4(b). Adherence to the ISNT rule is an important indicator for non-glaucoma, thus, any variation from this rule may help to detect glaucomatous damage. Medical image processing technology and statistical learning models are be used to identify and detect whether the optic rim follows the ISNT rule. This module uses the optic cup and optic disc obtained by the CDR module, and measures the four distances. This can be done by measuring the width and/or areas of the four regions defined based on the optic cup and disc obtained from the CDR module. Compliance with the ISNT rule is then detected.

5. Inter-Eye Asymmetry

Inter-eye asymmetry of cupping (a CDR difference 0.2 or greater; this number is obtained on the advice of clinical practitioners) may be useful to identify glaucoma because one eye is frequently more advanced than the fellow eye in glaucoma patients. Medical image processing technology such as color correction and euclidean geometry transformations is used to detect the asymmetry of cupping between patients eyes. This can use the optic cup and optic disc extracted by the CDR mocule as described above.

6. Parapapillary Atrophy (PPA)

PPA is the recession of the retinal pigment epithelium (RPE) into the choroid. PPA is divided into a central zone beta-PPA and peripheral zone alpha-PPA. Beta-PPA is characterised by visible sclera and choroidal vessels, extending from the sclera ring. Zone alpha-PPA is characterised by hyper- or hypo-pigmentation of the RPE. Beta-PPA (but not alpha-PPA) has significance in glaucoma, so this module of the unit 4 employs medical image processing methods such as level-set, histogram-based segmentation, edge detection and region growing are employed, relying on PPA-specific image cues and features such as color, contrast, roughness, texture, to detect the presence and extent of beta-PPA. Using the optic disc detected previously by the CDR module as the starting point, the image processing techniques are used to analyze the optic disc boundary, based on the previously mentioned images cues. Region-based knowledge of PPA localization based on clinical input is used to regulate the obtained results for PPA detection. Optionally, the PPA detection algorithm discussed under heading 2.3 below may be used.

A temporal crescent of alpha-PPA may be is present in about 80% of the normal population, however, in glaucoma, the frequency and area of PPA increases. The site of the largest area of atrophy tends to correspond to the part of the disc with most NRR loss. Beta-PPA is graded on the severity or extent of its presence. The available grading codes are 'mild', 'moderate', and 'extensive'.

Figure 5:
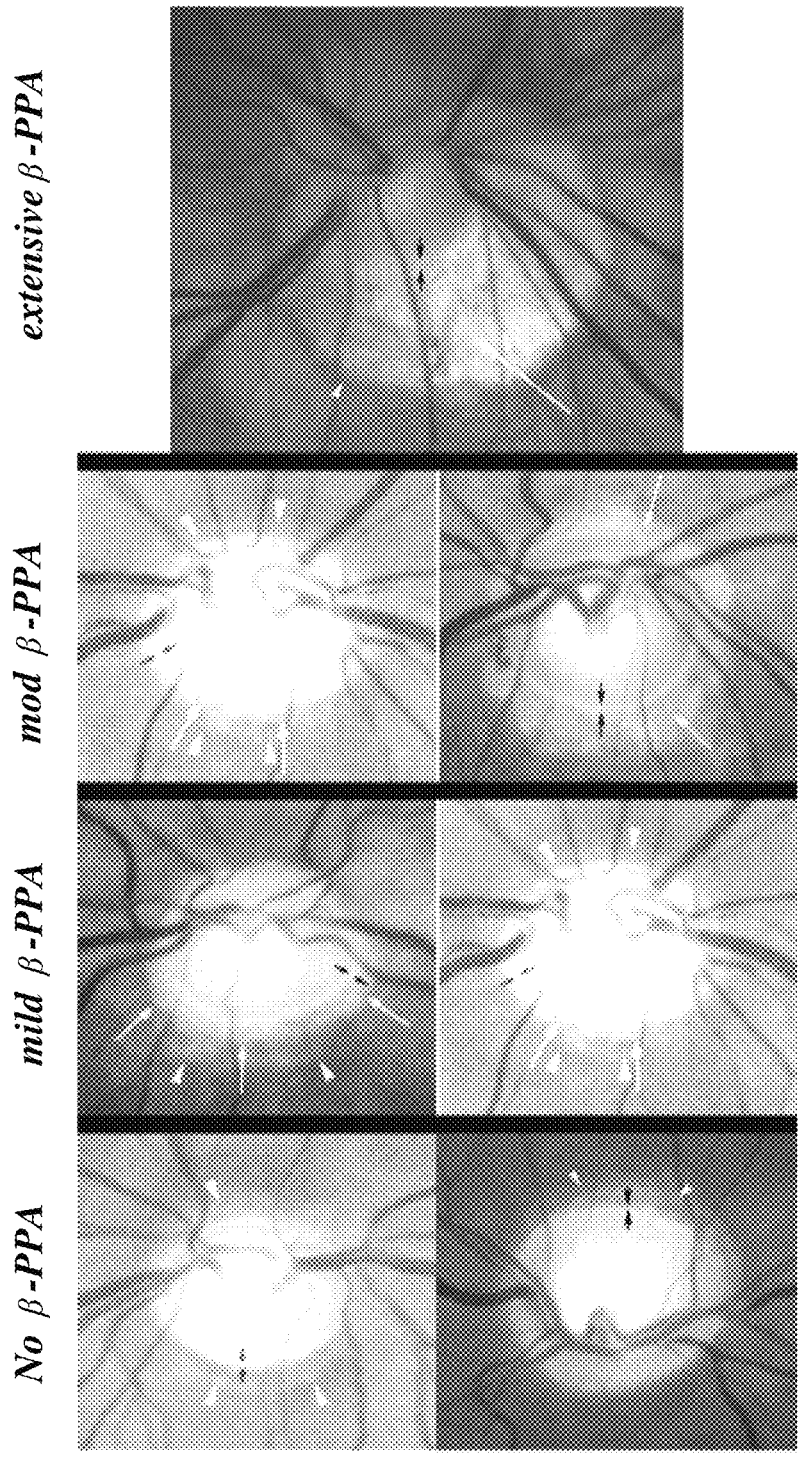
FIG. 5 illustrates a process employed by the embodiment of FIG. 2 for grading parapapillary atrophy (PPA)

FIG. 5 gives reference images for these grades, for the sake of illustration only. The two images in the left column exhibit no beta-PPA. The two images in the second column have mild-PPA. The two images in the third column have moderate beta-PPA. The image on the right of FIG. 5 has extensive beta-PPA.

7. Notching of the NRR

Neuroretinal rim notching is focal thinning of the rim which is another glaucomatous structural damage at the optic disc. Disc haemorrhages or RNFL defect often develop at the edge of the notch. Medical image processing technology are used to detect notching. First, the module applies a red-free filter to enhance the cup margin and RNFL appearance. Notch-specific edge detection, dedicated notch shape models and special variation of gradient changes are used to detect the notches. The presence of a 'notch' is recorded in relation to its location within the optic disc.

8. Blood Vessel Pattern Analysis

Retinal blood vessels can provide very useful information for the analysis of ocular diseases, including glaucoma. Wavelet analysis is be used to generate and analyze the blood vessel patterns. The main advantage of applying the wavelet analysis to the detection of edges in the retinal fundus image is the possibility of choosing the size of the details that are detected for vessel detection.

9. Blood Vessel "Kink" Analysis

Kinks are defined as the morphological bending of small blood vessels at the boundary between the optic cup and optic disc and are formed when small vessels cross over from the surrounding disc region into the depression formed by the optic cup. The locations of kinks are thus useful for the assessment of the border of the optic cup to determine the optic cup boundaries. This module makes uses of the techniques explained in [4] to detect scenarios of kinking. Specifically, in late glaucoma cases, the vessel kinking progresses to a form known as the bayoneting of vessels, which is defined as a sharp changes in vessel curvature. This phenomenon can indicate the presence of a deep optic cup implying glaucoma.

10. Disc Size Classification

Given that the NRR is made up the optic nerve fibres exiting the disc, a large disc may have a thinner relative NRR, or larger CDR than a smaller disc because the fibres are spread over a larger area. Therefore, a CDR of 0.7 in a large disc may be equivalent to a CDR of 0.4 in a small disc in Glaucoma diagnosis, as the same surface area of nerve fibres may be present on both discs. This module of the unit 4 automatically calculates the disc size from the optic disc obtained by the CDR module, and classifies it into large/medium/small categories.

11. Disc Tilting Analysis

Figure 6:
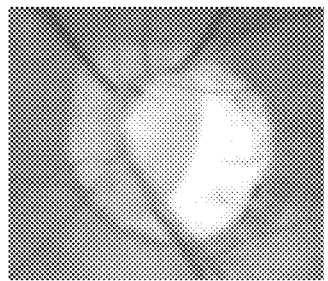
FIG. 6 illustrates the phenomenon of a tilted disc detected in the embodiment of FIG. 2.

The phenomenon of disc tilting means that the optic nerve extends to the retina at an oblique angle. When an optic disc is subject to disc tilting it often appears as illustrated in FIG. 6, that is, distorted with a distinct crescent of exposed sclera. Disc tilting often creates discrepancy in grading a fundus images as different graders. This module of the unit 4 measures the tilt angle based on the disc contour. The disc tilting analysis module uses the disc obtained by the CDR module. The optic disc, estimated by an ellipse, has a vertical major axis in a normal fundus image. The tilting angle can thus be calculated by finding the angle between the major axis of the disc and the vertical direction.

12. Gradeability

Based on both global and local analysis of the retinal image, the embodiment determines the gradeability of the images. This will help to provide an objective and repeatable analysis to the image. The gradeability of the fundus images will provide constraints and optimal parameters for the detection of the other image processing modules. The gradeability module can provide a score for the image gradeability, which is used to constrain the detection of other image cuts as well as to act as in input to the intelligent fusion unit 7. (Note: below, in section 2.1 we discuss another algorithm which obtains gradability: a "calibration module". However, the calibration module uses a different grading algorithm. The calibration module only decides whether a given image can be processed by the system or not.)

13. Retinal Nerve Fiber Layer (RNFL) Defect Presence Detection

In normal eyes, the RNFL appears as grey fibre bundle striations, unevenly distributed. The fibre bundles are most obvious in the inferotemporal sector, followed by the supero-temporal area, the supero-nasal region and finally the infero-nasal sector. They are least visible horizontally in the temporal and nasal regions. The embodiment provides, for at least some patients, automatic detection the presence or absence of RNFL based on image analysis. Making use of the special image features (color, shape, texture, etc), specific medical image processing technologies are developed to detect the presence of RNFL defects.

Having now finished describing the modules of the unit 4, we now describe the other modules of the system of FIG. 2.

The medical report 2 is input to a data mining module 5. The data mining module structures the input medical report (usually parsing it, adding some derived linguistic features and the removing of others, and subsequent inserting the result into a database), deriving patterns within the structured data, and finally evaluating and interpreting the output. The data mining module 5 is looking for high quality information. 'High quality' in text mining usually refers to some combination of relevance, novelty, and interestingness. Typical text mining tasks include text categorization, text clustering, concept/entity extraction, production of granular taxonomies, sentiment analysis, document summarization, and entity relation modeling (i.e., learning relations between named entities). Data mining techniques such as pattern matching, data modeling, features selection, classifications and correlation will be utilized.

The genetic data 3 is input to a GWAS module 6, which identifies SNPs of the subject and/or the levels of expression of one or more pre-defined genes. There are typically at least 3 such genes thought these may be a much higher number.

Certain genes have already been implicated in primary open angle glaucoma (POAG) by classical linkage studies, but these studies suggest that they contribute to the pathogenesis of POAG in less than 5% of cases in the general population. Genes accounting for a more significant proportion of the known heritable component of glaucoma remain to be identified, such as by a GWAS study.

Specifically, the pre-determined genes and/or SNPs may be identified in advance by performing a large scale genome wide association (GWA) study for various glaucoma characteristics, to identify and characterize potential glaucoma-related genes and SNPs. Statistical analysis may be used to find genetic markers with the strongest association with glaucomatous optic nerve features, such as the 13 structural features identified by the unit 4. That is, the study may link the genetic information with a comprehensive set of phenotypes, including various image cues detected by the 13 above mentioned methods, such as CDR and PPA.

A case-control study population is formed from various cohorts: the glaucoma cases and normal controls. A single-stage GWAS and the appropriate statistical analyses can identify correlation between genetic changes (SNPs) and the incidence of glaucoma, and further determine the Genetic Map position to locate the identified SNPs on the exon, promoter or enhancer region.

Genotyping data from multiple population groups may be used in this study, such as a database of the Singapore Malay population, the Singapore India population and the Australia Caucasian population. The results from 3 different populations may be compared and consolidated, to find replicable associations.

The outputs of all these units 4, 5, 6 are input to an intelligent fusion module 7, such as a multi-layer neural network. The output of the neural network is a glaucoma risk assessment result 8 of the system. The parameters of the neural network 7 are trained using a large collection of retinal fundus images. In this way, this neural network learning mechanism integrates the knowledge embedded in the clinical practice. Other machine learning techniques which may be used in this intelligent fusion module include Support Vector Machines (SVM) and AdaBoost.

The glaucoma risk assessment report 8 may be generated in a format for easy reading and understanding for patients and doctors. The report also documents and consolidates the patient-specific's results and findings from the units 4, 5 and 6.

The embodiment can be validated using a database such as a collection of 15,000 clinical eye data available to us collected from different races (Chinese, Malays, Indians, Whites) and countries (Singapore and Australia), the first such database in the world. This was collected by workers at SERI/SNEC and Australia (from Melbourne and Sydney), comprising 15,000 persons (with 750 glaucoma cases) from the Singapore Malay Eye Study (SiMES), the Singapore Indian Chinese Cohort Eye Study (SICC) and the Blue Mountains Eye Study (BMES), Australia. All 15,000 persons have clinical and detailed characterization of glaucoma. Approximately 10,000 persons in this cohort have GWA data (610K Illumina chip) available for analysis. The database is suitable for performing the GWAS study.

The embodiment is suitable for readily implementation in currently available instruments for ocular screening without extensive modifications.

2. Optional Features of the Embodiment

As described above, FIG. 2 denotes the embodiment with the cup and disc identification functions as part of the unit 4. It is alternatively possible to denote the first embodiment by the diagram of FIG. 7, which is the same as FIG. 2 except that it additionally includes a toolbox unit 9 which provides services for the modules of the unit 4. These services include functions such as the task of identifying the optic disc and/or optic cup. In other words, in this representation of the first embodiment, the optic disc and/or optic cup detection processes are performed by the toolbox 9, and the CDR module of the unit 4 merely receives the results and produces the CDR result by applying the adaptive model described above. Other modules of the unit 4 can also make use of the optic cup and disc estimate produced by the toolbox 9.

This section of the document describes four additional optional features of the first embodiment. It is most convenient to consider these four optional features using a diagram of the form of FIG. 7. The toolbox unit 9 includes respective modules for performing respective functions to implement the four optional features. As will be seen, the first three of these features relate to services which the toolbox 9 performs for the unit 4. The last relates to a communication which the toolbox 4 implements between the unit 4 and the GWAS module 6. Also illustrated in FIG. 2 are optional interactions between the data mining unit 5 and the unit 4 and/or the GWAS module 6.

2.1 Intelligent Calibration

A first module of the toolbox 9 may be one which performs intelligent calibration. Intelligent calibration means that the images 1 are processed before being input to the unit 4. There are several reasons why this may be valuable.

For example, it may be useful to screen the input images. One potential problem we have identified with the embodiment is that it may fail in extreme cases. For example, the cup detection algorithm may not be able to locate the cup correctly for images with extremely small or extremely big cups. Also, the embodiment as described above processes images with poor quality in the same way as images with good quality. The results from such images are quite poor and can cause noise in the result analysis. The intelligent calibration module of the unit 9 classifies the images 1 into gradable or non-gradable images before they are input to the unit 4. Poor quality images are not processed by the system. Instead, they are placed in a special database for clinician's attention, for example because they may exhibit signs of other eye diseases. Only the gradable images are input to the unit 4, where they are processed for disc and cup segmentation.

Also, a variational level set algorithm, of the type used in the cup detection module process of the embodiment, uses several parameters that can affect the evolution of the level set function. Using the same parameter values for different images produce inaccurate result for extreme cases. The calibration module may calculate suitable parameter values for each individual image. The methods used to determine the parameter values are histogram analysis and adaptive thresholding.

Figure 8:
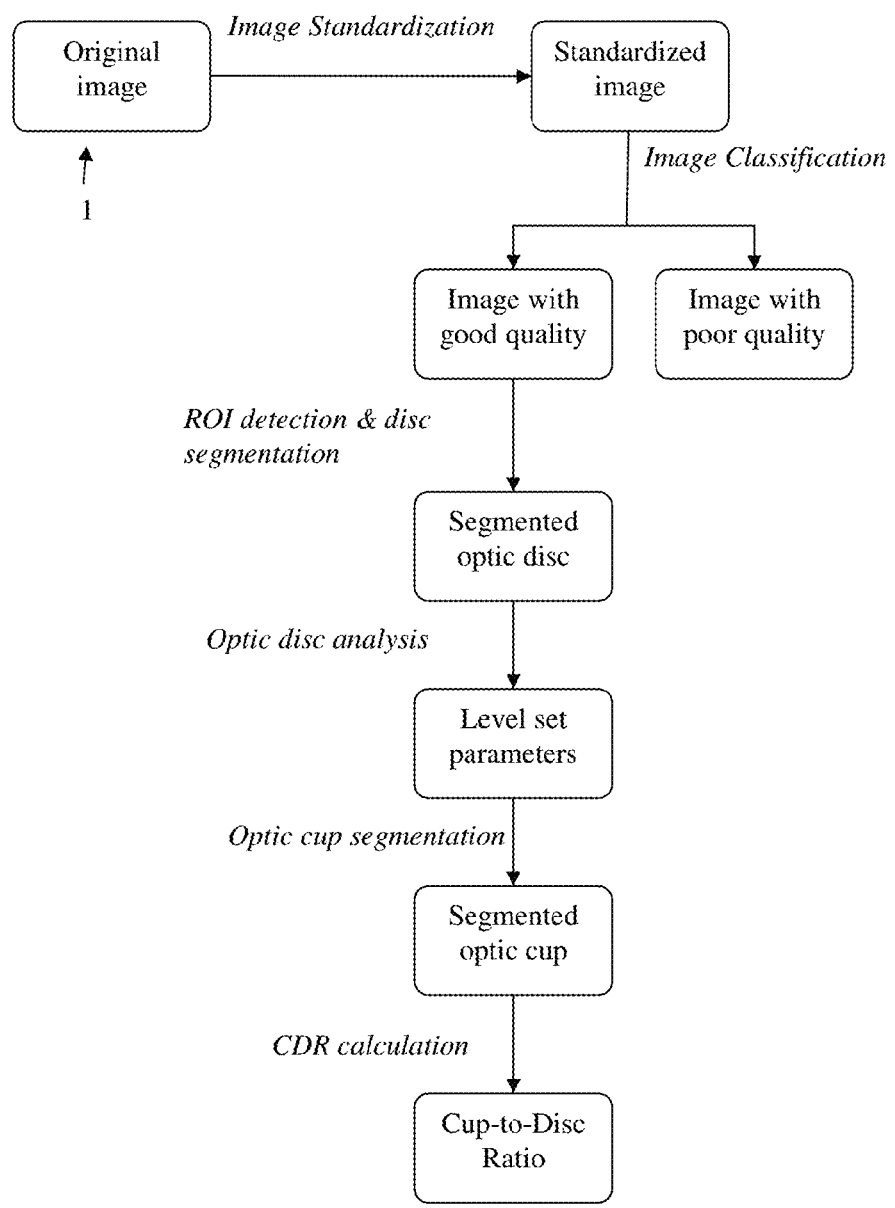
FIG. 8 is a flow diagram of a process performed by a portion of the structure of FIG. 7.

FIG. 8 shows the method performed collectively by the calibration module of the toolbox 9 and the CDR module of the unit 4.

2.1.1. Image Standardization

In a first step ("image standardization") the calibration module performs standardization and classification on the image 1. Retinal fundus images can be taken by different cameras with different settings. Retinal image databases such as Singapore Malay Eye Study (SiMES), Retinal Vasculature Glaucoma Subtype Study (RVGSS), Singapore Indian Chinese Cohort (SICC) Eye Study and Blue Mountains Eye Study (BMES) are famous eye study databases. Images in these databases have different resolutions due to different camera settings. FIGS. 9(*a*)-(*d*) show sample images of these databases. Specifically, FIGS. 9(*a*)-(*d*) are images from the SiMES, RVGSS, SICC, and BMES databases respectively.

In this step, all images are standardized to the same resolution of images in SiMES database, which is 3072 by 2048 pixels. This process is valuable since otherwise the images may not be properly processed by the trained models in the steps which follow.

2.1.2. Image Classification

Some of the images are of poor quality due to the existence of cataract or focusing issue. In a second step ("image classification"), the images are classified to reduce the possibility of wrong detection. Texture analysis is done to classify the images to gradable or non-gradable. FIGS. 10(*a*) and (*b*) show respectively images which classified as gradable and non-gradable.

Figure 11:
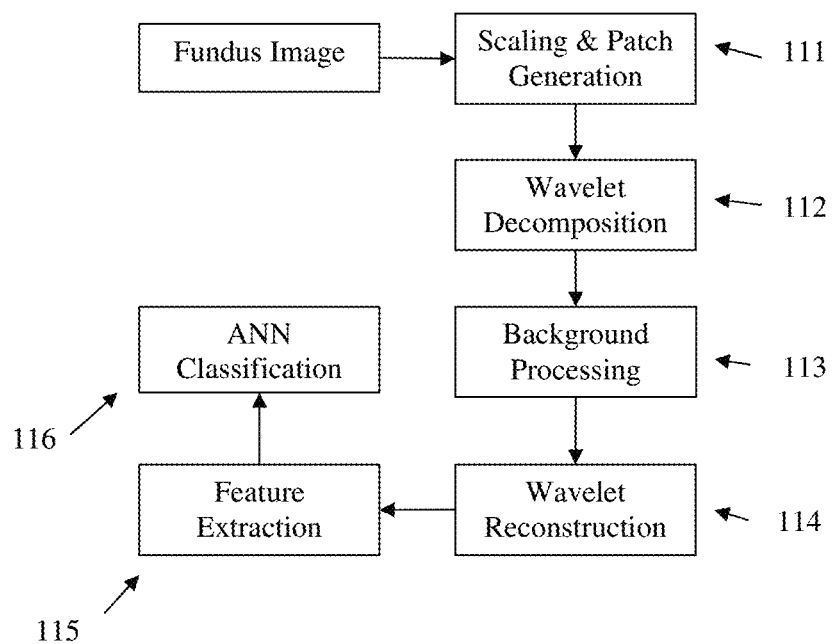
FIG. 11 is a flow diagram of a step used in the process of FIG. 8.

FIG. 11 shows the steps of classifying images based on image texture. Image texture is defined as a function of the spatial variation in pixel intensities. It is the most important visual cue in identifying different type of homogeneous regions. Firstly, in step 111, the fundus image is scaled and small patches are generated. Wavelet decomposition (step 112), background processing (step 113) which means image background processing (by setting the background intensity to a certain value, the desired features can be observed more easily), and a reconstruction (step 113) are then applied to discriminate different frequencies and preserve certain image details. Subsequently, features are extracted from the processed patches (step 114). Finally, in step 115 a Artificial Neural Networks (ANN) is used to classify the images. The ANN has previously been trained based on data obtained (by performing steps 111-115) on training images which are pre-known to be of high and low quality.

The non-gradable images are not processed by the system. They are placed in a special database for clinician's attention of other eye diseases. Gradable images will be processed for disc and cup segmentation, in the following steps.

2.1.3. ROI Detection and Disc Segmentation

In a step of "ROI detection and disc segmentation", a region of Interest (ROI) is detected by performing fringe removal. Subsequently, an image is divided into multiple sub-regions and intensity analysis is applied to each sub-region to find the desired sub-regions to form the ROI. Then disc segmentation is performed using an active shape model (ASM). Both steps are just as described above in the description of the CDR module.

2.1.4. Optic Disc Analysis

There is then a step of "Optic disc analysis", performed by the intelligent calibration module of the toolbox 9, in which a level set algorithm is used to generate parameters. These parameters are very useful for the unit 4. Experimental results show that the CDR module of the unit 4 uses the ARGALI algorithm [2] as described above, it tends to overestimate CDR for images with very small CDR and underestimate CDR for images with very high CDR. This is due to the limitation of the gradient and intensity approach of the cup detection method. It employs a variational level set method which initializes from a threshold. In the case of an extremely large or small cup, the gradient values are gradual, resulting in difficulties in identifying the cup. One key factor that affects the detecting accuracy is the initial contour of the level set evolution which is initiated by thresholding. The thresholding method used in the ARGALI method [2] is P-tile thresholding which chooses the threshold value to be the intensity value that corresponds to ⅔ of the cumulative sum of pixel intensities. This thresholding method is not robust enough for all images. The intelligent calibration module uses a more robust thresholding method for the initialization process. Adaptive thresholding (which changes the threshold dynamically over the image) and histogram analysis are used to determine the threshold value.

2.1.5. Optic Cup Segmentation

There is then a step of "Optic cup segmentation". Optic cup segmentation is the most critical part of the ARGALI algorithm. A variational level set that is initiated from a threshold is used for cup segmentation in ARGALI. The threshold value that is generated in the optic disc analysis step (step 2.1.4) can result in more robust segmentation than fixed threshold one.

We now present experimental results from using the intelligent calibration module. 75 images from Retinal Vasculature Glaucoma Subtype Study (RVGSS) database and 310 images from Singapore Indian Chinese Cohort (SICC) Eye Study database were tested by a system which included the unit 4 and a toolbox 9 with an intelligent calibration module as described above. The experimental results show that 38.2% of the images failed to be processed correctly by the unit 4 alone because 83.1% of the images are non-standard images. By contrast, the combination of the unit 4 and the intelligent calibration module processed 100% of the images, which demonstrates better generality and robustness. The cup-to-disc ratio estimation is also improved by adding the calibration module.

In summary, the calibration module, unlike all the prior art systems described above, is capable of operating with multiple image formats, and is compatible with multiple databases with different respective image formats. Furthermore, unlike the prior art methods, it can automatically identify and reject non-gradable images. Thus, the intelligent calibration module enables a more robust way to process images and is more suitable to apply to the general population.

2.2 Spatial Heuristic Ensembling

In the embodiment as described above, several techniques are used to optic cup detection (e.g. the technique used by the ARGALI algorithm, and the technique using kink analysis). Each technique stands individually, and is assessed on its own performance, after which the best performing technique is used for optic cup detection. Although some techniques offer some advantages over others in specific regions of the image, this is not taken into consideration.

Figure 12:
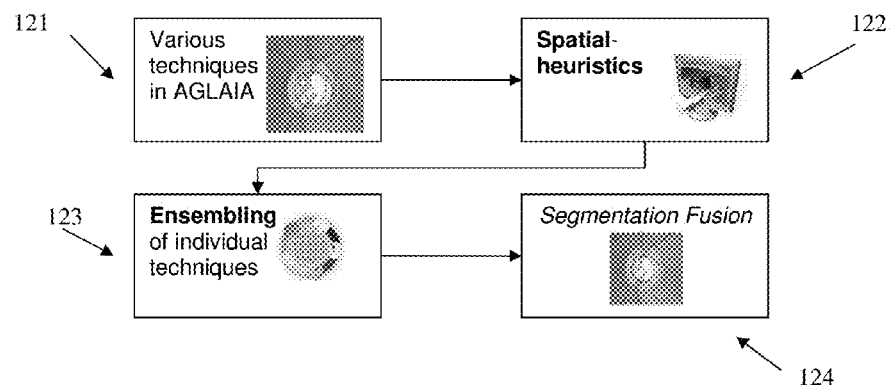
FIG. 12 is a flow diagram of a SHE module used in the structure of FIG. 7.

In this variation, the toolbox 9 includes a Spatial Heuristic Ensembling (SHE) module to combine the results of different optic cup detection methods ('ensembling') through the use of prior knowledge in the segmentation performance ('heuristics') for specific regions ('spatial') in the images to be processed. SHE is a post-processing framework that aims to optimize segmentation performance of the optic cup by combining salient advantages of each method in a region-based approach. A flowchart of the SHE is shown in FIG. 12.

A first step 121 of the process is the segmenting the optic cup by multiple methods, which include a color histogram analysis, the level set method of ARGALI [2] and the kink analysis method of [4].

2.2.1 Spatial Heuristics

The result is input to the SHE module of the toolbox 9, which first performs a spatial heuristics step 122 of analyzing the results of each different technique used for the specific task of segmenting the optic cup. This step is performed for each image. It finds which segmentation technique is likely to be best at each angular position around the optic cup, based on ground truth evaluation. In the absence of ground truth, the best segmentation technique can be determined based on previously generated models and an understanding of the optic cup morphology.

Figures 13A, 13B:
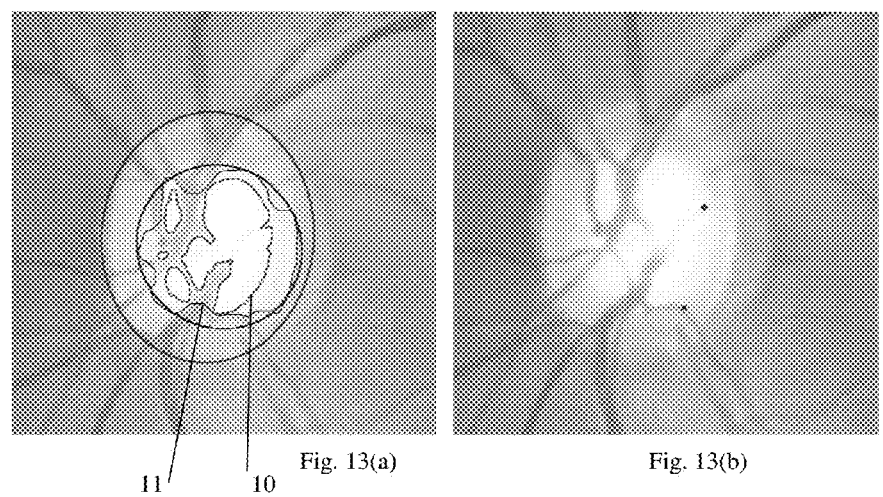
FIG. 13(a) shows the results of two techniques for optic disc segmentation.
FIG. 13(b) shows two positions with blood vessel kinks.

Shown in FIG. 13(a) are examples of two different methods, based on color histogram analysis (CH, marked as the contour 10 and variational level-set based segmentation (LS, marked as contour 11). Comparing against the ground truth results, it can be seen that the LS gives a better overall segmentation, in particular on the nasal side of the image. However, LS tends to be over-aggressive in the temporal side, under-segmenting that region. CH does not perform as well as LS, with a more conservative segmentation. However, it can be seen that the on the temporal side, the CH results tend to be more reliable than LS. Such a trend is generally observed on the images tested. Selecting one over the other would be disregarding the inherent advantages of each.

We have also used kink detection [4] as a way to demarcate the cup boundary, as indicated by the bending of vessels due to the topology change in the optic nerve head due to the cup excavation. Kinks are illustrated by the dots of FIG. 13(b). However, kinks are not present in all images.

2.2.2 Ensembling of Techniques

Based on the spatial analysis performed in the previous step, an understanding of the cup segmentation techniques used can be obtained based on the overall segmentation performance trends and spatial bias of the results. Re-iterating the previous analysis, LS tends to segment the nasal region of the image well, while undersegmenting the temporal region. In contrast, CH tends to give a better segmentation result in the temporal region. The two techniques complement each other well, and this understanding can be embraced to fuse the two techniques together. A number of fusion paradigms can be designed. We describe examples in the following (1) Sectoral Paradigm Model In this model, the region is divided into two or more sectors, with each sector defined by and utilizing the relevant optimal technique for that sector based on the prior spatial analysis. Based on the spatial analysis from the optic cup segmentation in AGLAIA, we can divide the potential cup location within the optic disc into two distinct regions, nasal and temporal. On these regions the results from the better performing technique is used, obtaining a fusion of results better than from each individual method.

A simple example is given in FIG. 14(a). In the left hand side of FIG. 14(a) (the temporal side), the CH is used. In the right hand side of FIG. 14(a) (the nasal side), the LS algorithm is used.

More generally, the following are specific examples of how such a method can be implemented.

First consider only two individual techniques for optic cup segmentation. Let the results of technique 1 be $T_1$ and technique 2 be $T_2$, where $T_1$ refers to the region segmented by $T_1$, and $T_2$ be the region segmented by $T_2$ and define the segmentation results in polar coordinates centered at the optic disc centre. If $T_1$ is optimal for the interval $\Delta\theta_1$, and $T_2$ is optimal for the interval $\Delta\theta_2$ based on empirical prior heuristic observations $\theta \in \Re$, $0 \le \theta \le 2\pi$ and assuming non-overlapping regions where $\{\Delta\theta_1 \cap \Delta\theta_2 = \phi\}$, a possible implementation of SHE can be seen by the following expression, where S refers to the region of selected pixels $$S = y_1 T_1 + y_2 T_2,$$

where $$\gamma_1 = \begin{cases} 1 & \text{for } \theta \subseteq \Delta\theta_1 \\ 0 & \text{otherwise} \end{cases}, \gamma_2 = \begin{cases} 1 & \text{for } \theta \subseteq \Delta\theta_2 \\ 0 & \text{otherwise} \end{cases}$$

If the two techniques overlap such that $\{\Delta\theta_1 \cap \Delta\theta_2 = \phi\}$ $$\gamma_1 = \begin{cases} \alpha_1 & \text{for } \theta \subseteq \Delta\theta_1 \\ 0 & \text{otherwise} \end{cases}, \gamma_2 = \begin{cases} \alpha_2 & \text{for } \theta \subseteq \Delta\theta_2 \\ 1 & \text{otherwise} \end{cases},$$

$$\alpha_1, \alpha_2 \in \Re; \alpha_1, \alpha_2 \ge 0$$

where $\alpha_1$, $\alpha_2$ are parameter values that can be set based on the heuristic observations on prior heuristic knowledge, and can be useful in selecting between overlapping results.

These parameter values can be obtained from training data, or from instance-based estimations.

For a more general case, where there are N techniques, each technique $T_n$ optimal for a subrange $\Delta\theta_n$ $$S = y_1 T_1 + y_2 T_2 + \ldots + y_n T_n + \ldots y_N T_N, n \in \Re; n = \{1 \ldots N\}$$

and $$\gamma_n = \begin{cases} \alpha_n & \text{for } \theta \subseteq \Delta\theta_n \\ 0 & \text{otherwise} \end{cases}, \alpha_n \in \Re; \alpha_n \ge 0$$

(2) Clockface Paradigm Model

Another model for consideration is to fuse the individual results by utilizing lines of interest emerging from the centre of the optic cup which have equal angular separation. This is illustrated in FIG. 14(b). This model is useful for fusing boundaries obtained from different techniques, based on comparing the how each technique performs along each line of interest. The optimal performing technique for each line is chosen. By careful selection of the lines of interest and angular separation, poor performing sectors for the techniques under test can be filtered out. The implementation can be similar to (1) above, where S now indicates points at specific angular separation $\Delta\theta$ and rather than a region or grouping of points.

(3) Modified Clockface Paradigm Model

To include kinks in the analysis, we make use of a modified clockface paradigm model. Defining the centre of the region as the disc centre, we utilize the results from the level set method for the nasal half of the cup. In the temporal half, any kinks are first determined on the model. Subsequently, any remaining gaps are filled using the results from the color histogram technique.

The models (1)-(3) are examples of the types of fusion paradigms that can be used in SHE. The selection of the paradigms can be carried out manually based on the prior knowledge and experience of the segmentation performance. Alternatively, machine learning techniques such as support vector machines, or neural networks, can be implemented to learn the optimal design and selection for technique fusion. In addition, for techniques which overlap, a weighted decision making process can be used, and the weights can also be learnt in this step.

2.2.3 Results Fusion

After the heuristic information has been obtained and the fusion paradigm has been designed, either manually or through the assistance of machine-learning methods, the fusion paradigm can be utilized to ensemble the results obtained from the various techniques evaluated. Each image to be segmented is processed using the various techniques individually first. Subsequently, the results are saved and passed to the fusion paradigm. Based on the spatial heuristics obtained earlier and the fusion paradigm selected, the segmentation results will be combined in step 124 in a complementary manner to form an optimal segmentation of the optic cup. This entire process is automatically done without user intervention.

FIGS. 15(a) and (b) show experimental results from testing the SHE module. In each image, the ground truth is indicated as 12, the result of the LS segmentation as 13 and the result of the SHE module as 14. In FIG. 15(b), the contours 12 and 14 are almost indistinguishable.

To further evaluate the performance of the SHE module, a sample of 67 retinal fundus images was obtained from the Singapore Eye Research Institute. Each image has a resolution of 3072×2000, and was collected under typical clinical conditions as part of the Singapore Malay Eye Study. A senior ophthalmologist manually determined the optic cup and disc using a customized graphical tool, using only the retinal fundus image itself without knowledge of pre-existing physiological or medical conditions, or the use of other imaging modalities. These were denoted as the cup and disc reference segmentations for each retinal image. The same set of retinal images was also independently assessed for the cup and disc contours by a group of experienced graders, which acted as a "second observer" for the identification of the optic cup and disc in the image set.

To provide a quantitative measure of the accuracy of optic cup, we made use of two segmentation metrics, previously used to assess the performance of volumetric 3D liver tumour segmentation techniques, and modified the terms to consider area instead of volume. The area overlap error, $m_1$, is defined as $$m_1 = \left(1 - \frac{\text{Area}_{seg} \cap \text{Area}_{ref}}{\text{Area}_{seg} \cup \text{Area}_{ref}}\right) \times 100\%$$

where $\text{Area}_{seg}$ indicates the segmentation results, and $\text{Area}_{ref}$ denotes the ground truth segmentation. The area overlap error metric is an indicator of how well the segmented area matches with the reference area, with a value of '0' being perfect segmentation. Another metric used is the relative area difference $m_2$, defined as $$m_2 = \frac{\text{Area}_{seg} - \text{Area}_{ref}}{\text{Area}_{ref}} \times 100\%$$

which indicates if a segmentation is under- or over-segmented by its sign ($m_2>0$: under-segmentation; $m_2<0$: over-segmentation) and the extent of area difference by its magnitude with a value of 0 indicates no error in the size of the segmented area.

Using $C_{SHE}$ to indicate the optic cup detected using SHE, $C_L$ to indicate the optic cup detected using the best performing individual method based on level set only, the automatic segmentations for each retinal image were evaluated against the corresponding reference segmentation using the previously defined measures. The results were then calculated for each retinal image, averaged across all the images as $M_1$ and $M_2$, and are tabulated in Table 1. The average of the absolute values of $m_2$ is also included to obtain the average magnitude of segmentation error, represented as $M_2^A$. $C_{SHE}$ tends to over-segment the optic cup $M_2(C_{SHE})<0$ while $C_L$ tends toward under-segmentation $M_2(C_P)>0$. However, $C_{SHE}$ has a lower overlap error $M_1(C_{SHE})<M_1(C_L)$ and a better estimation of the optic cup size $M_2^A(C_{SHE})<M_2^A (C_L)$. When $M_1$, $M_2$ and $M_2^A$ are calculated for $C_{SHE}$ and $C_L$ with respect to the 'second observer', a similar trend of results is obtained. To determine the difference in the inter-observer cup segmentations, the segmentation comparison metrics were calculated between the reference and 'second observer' segmentations. The results show a similar magnitude of difference between the two manual segmentations, suggesting that results are comparable to an independent observation.

Next, we compare the dimensions of the automatically detected optic cup segmentations with respect to the reference segmentation. The physical dimensions were converted from pixel dimensions using a scaling value obtained from the retinal camera manufacturer. We calculated the root mean square error (RMSE) of the detected dimensions with respect to the reference dimensions and also calculated the intra-class correlation coefficient (ICC), to assess the consistency of measurements. The results of the RMSE and ICC analysis are tabulated in Table 1. For $C_{SHE}$, a RMSE of 0.17 mm was calculated for both dimensions, with corresponding ICC values of 0.65 and 0.71 for height and width respectively. This is considerably better than for $C_L$ [RMSE: 0.18 mm (height), 0.30 mm (width); ICC: 0.56 (height), 0.53 (width)], which tends to over-estimate the optic cup, particularly in the horizontal. Through the use of the SHE framework in the detection of the cup, a 43.3% reduction in the error of the cup width was achieved.

TABLE 1

Results of comparison between different methods for optic cup segmentation.
RMSE and ICC results are presented for (cup height, cup width)

| | Segmentation metrics | | | | | |
|---|---|---|---|---|---|---|
| | (wrt ground truth) | | | (wrt $2^{nd}$ observer) | | |
| Method | $M_1$ | $M_2$ | $M_2^A$ | $M_1$ | $M_2$ | $M_2^A$ |
| $C_{SHE}$ | 28.45 | −7.04 | 21.11 | 28.73 | −2.29 | 17.2 |
| $C_L$ | 37.75 | 33.57 | 36.96 | 41.67 | 41.1 | 44.04 |
| Inter-observer | 22.6 | −5.6 | 16.76 | | | |

| | Dimensions | | | |
|---|---|---|---|---|
| | (wrt ground truth) | | (wrt $2^{nd}$ observer) | |
| Method | RMSE | ICC | RMSE | ICC |
| $C_{SHE}$ | (0.17, 0.18) | (0.66, 0.73) | (0.17, 0.19) | (0.64, 0.65) |
| $C_L$ | (0.18, 0.30) | (0.60, 0.59) | (0.26, 0.28) | (0.41, 0.57) |
| Inter-observer | (0.21, 0.10) | (0.64, 0.81) | | |

Figure 16:
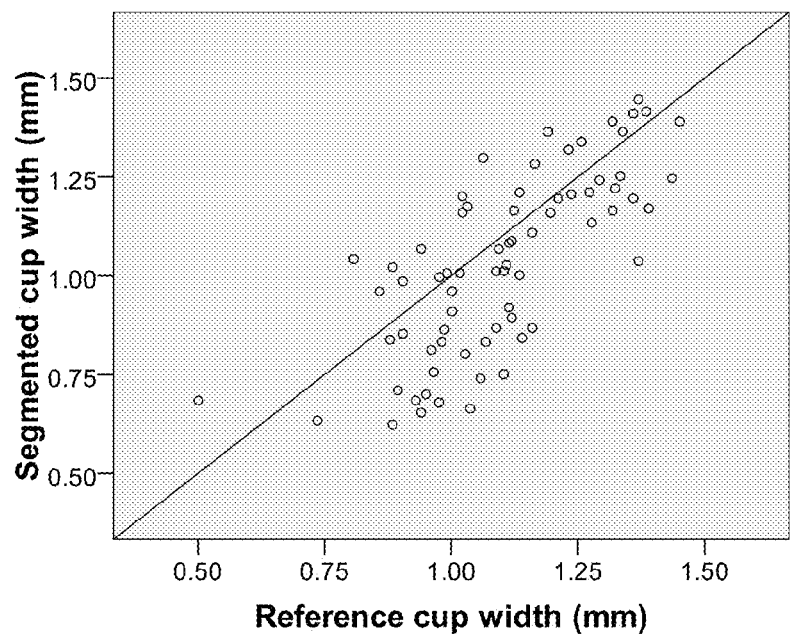
FIGS. 16(a) and 16(b) compare respectively the width and height of the optic cup obtained by the SHE module of FIG. 12, and a reference segmentation.
Figure 16:
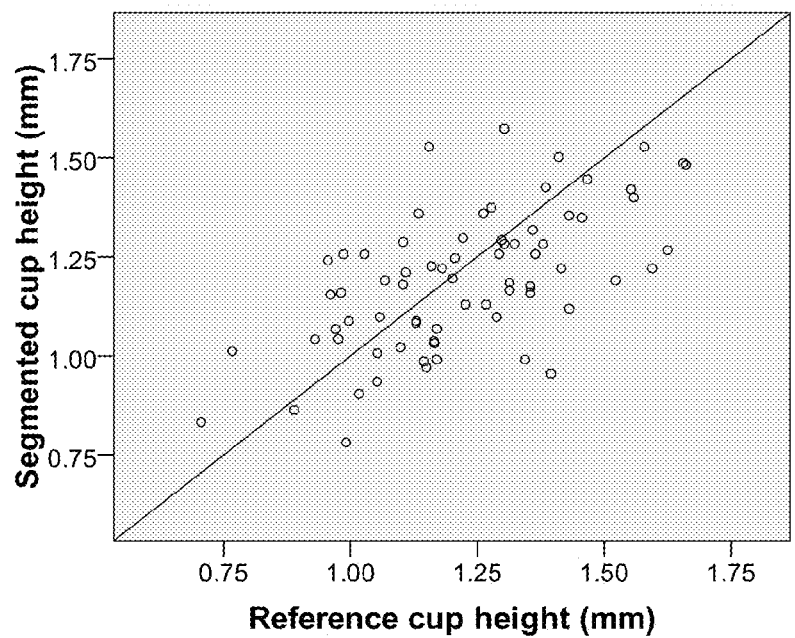

FIG. 16(a) shows a comparison of the optic cup width (100=0.66), and FIG. 16(b) shows a comparison of the optic cup height (100=0.73) for the SHE method and reference segmentation.

2.3 Optic Disc Segmentation Using Preliminary Retina Structure Segmentation

Whereas the SHE module of the toolbox 9 was for better segmentation of the optic cup, this section of the document describes an enhanced optic disc segmentation module of the toolbox 9.

Parapapillary atrophy (PPA) is the recession of the retinal pigment epithelium into the choroid. Sometimes PPA with a color similar to the optic disc introduces edge pixels which may be mistaken to be the disc boundary. As described above, several approaches have been proposed to segment the optic disc, such as the level set technique ARGALI of [2], which may be used in the embodiment of the invention. One limitation of the level set approach is that the disc boundary is often affected by a large number of blood vessels entering the disc. PPA and other structures often slow down the evolution of the level set to reach the disc boundary. Other methods to detect the optic disc use deformable models, but these approaches are sensitive to poor initialization. Moreover, these approaches are often fooled by PPA which forms an ellipse boundary as well. In some methods, the optic disc is approximated to be a circle. However, as has been shown in [2], the optic disc is often an ellipse instead of circle. A circular approximation is not good enough to segment the disc boundary accurately for computing CDR. As the disc boundary is not the only strong boundary, a Hough transform using all edge pixels detected by traditional edge detection algorithms such as 'Sobel' or 'Canny' edges often produces un-desired results [8].

The enhanced disc segmentation module selects which edges are used for disc segmentation, and fits an elliptical model of the optic disc to the selected edges. Specifically, preliminary retina structure segmentation is used to reduce the number of edges arising from boundaries which are not due to the optic disc, so that the ellipse detection can be more reliable.

Figure 17:
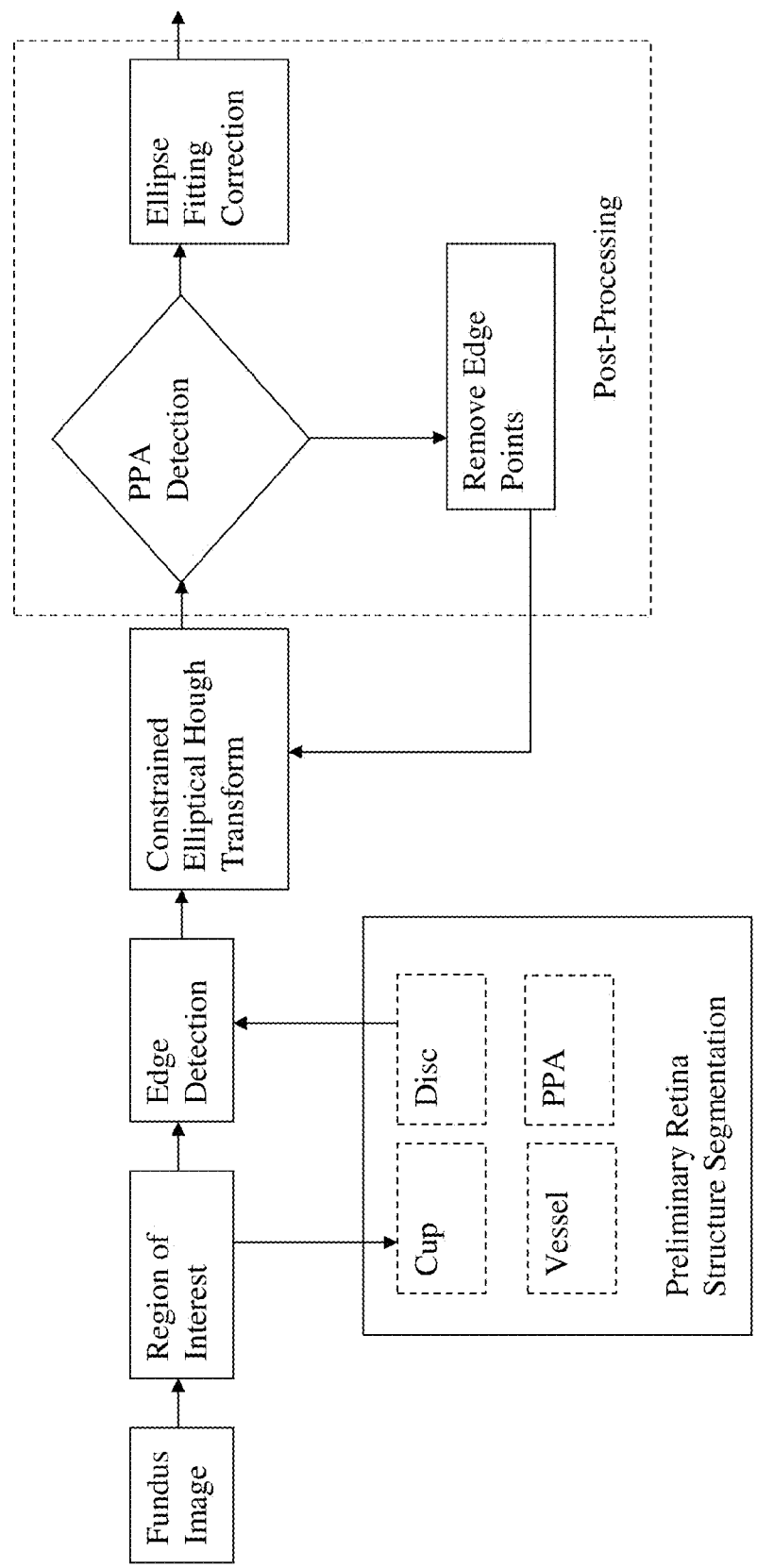
FIG. 17 illustrates the method performed by an enhanced disc segmentation module used in the structure of FIG. 7.

The framework of the segmentation is summarized in FIG. 17. Following region of interest (ROI) detection, it includes an edge detection step to find candidate disc boundary pixels; a preliminary retina structure segmentation (PRSS) step to reduce edges from non-disc boundary; an ellipse detection step to find the best fitting disc boundary; a post-processing process including a PPA detection step and an ellipse fitting correction step to refine the disc boundary.

2.3.1.1 Region of Interest Detection

The fringe removal based method in [9] [10] is used to extract the ROI. In the method, the fringe is first trimmed away from the fundus image. Next, the area where 0.5% of the brightest spot concentrated in the trimmed image is located. The centroid of the bright spot is marked as the center and a square with edge length twice the typical optic disc diameter is drawn at the center to determine the boundary of the ROI.

2.3.1.2. Edge Detection

There are mainly four structures with relatively strong edges in the ROI: disc, cup, blood vessel, and PPA. For disc segmentation, one would like to find the disc edges as much as possible while excluding edges from other structures. Sobel edge detection is used in [8]. The authors have shown that the Sobel edge performs better than Canny edge. Although these traditional edge detection algorithms might have been optimized for edge detection, for detecting the disc boundary it would be preferable for only the edges associated with the disc to be detected. One relevant observation is that the contrast in the optic disc boundary varies widely, not only from one image to another but also from one side of the disc to another side within the same image. For example, the edges from nasal and temporal sides are often more obvious than those from the inferior and superior sides.

1) Horizontal and Vertical Edges:

We use horizontal edges to determine nasal and temporal boundaries, vertical edges to determine inferior and superior boundaries. The horizontal and vertical edges are obtained as follows.

Let us denotes the M×N ROI as l with its pixel values l(x, y), 1≤x≤M, 1≤y≤N. First, one pixel within the disc is located. One of the ways of doing this is to use the geometric center (xc, yc) of the ROI. Then, the edge detection is done by detecting edges from each row and column of the image. Let us denote the ith row in the ROI by $L_i(y)=l(i, y)$, $y=1, 2, \ldots, N$. A smoothing process is first applied to reduce noise. Specifically, a mean filter is used to obtain:

$$\overline{L}_i(y) = \frac{1}{2J+1} \sum_{j=-J}^{J} L_i(y+j) \quad (1)$$

where 2J+1 is the length of the mean filter. Then the K preceding and K subsequent rows are used to compute a mean line $$\overline{\overline{L}}_i(y) = \frac{1}{2K+1} \sum_{j=-K}^{K} \overline{L}_{i+j}(y) \quad (2)$$

The first derivative $\overline{\overline{L}}_i'(y)$ of the mean line is obtained. For pixels on the left of center, i.e. $y \leq y_c$, we take the local maxima of $\overline{\overline{L}}_i'(y)$ as the possible disc boundary, for pixels on the right side, we take the local minima of $\overline{\overline{L}}_i'(y)$. Define $l\ max(v,T)$ as the operator to obtain the local maxima greater than T from a vector v. The set of the all detected local maxima is $S_{l\ max}^{h} = \cup_{i=1}^{M} l\ max\ (\overline{\overline{L}}_i'(y),T)$. Local minima of a vector v can be obtained by detecting local maxima of −v, thus, the set of the local minima is $S_{l\ min}^{h} = \cup_{i=1}^{M} l\ max(-\overline{\overline{L}}_i'(y),T)$. These local maxima and minima are possible edge points from the optic disc boundary. Two matrix $E_h^{max}$ and $E_h^{min}$ are obtained:

$$E_h^{max}(x, y) = \begin{cases} 1 & \text{if } (x, y) \in S_{lmax}^{h} \\ 0 & \text{otherwise} \end{cases} \quad (3)$$

$$E_h^{min}(x, y) = \begin{cases} 1 & \text{if } (x, y) \in S_{lmin}^{h} \\ 0 & \text{otherwise} \end{cases} \quad (4)$$

Similarly, we obtain $E_v^{max}$ and $E_v^{min}$ based on local maxima and minima from all columns. We set J=12 and K=5 experimentally based on wide variety of images. Finally, a binary map E is obtained as follows:

$$E(x,y) = E_h^{max}(x,y) + E_h^{min}(x,y) + E_v^{max}(x,y) + E_v^{min}(x,y)$$

where '+' is the 'or' operation.

2) Multi-Level Threshold:

A threshold T is used in the local maximum/minimum detection to reduce the amount of edge pixels due to noise. This is compared with the value of $\overline{\overline{L}}_i'(y)$ at the maxima/minima, computed based on equation (1) and (2), i.e. the first derivative of a smoothed intensity, at the maxima/minima. However, it is difficult to find a general value for a wide variety of disc boundary contrast from images of various qualities. The enhanced disc segmentation module uses a multi-level threshold to adopt the boundary to take into account different contrasts in different images. In the multi-level threshold approach, we define multiple thresholds $T_k$, k=1, 2, . . . , K k=1, 2, . . . , K, with $T_1 > T_2 > \ldots > T_K$. If the current threshold $T_k$ is greater than all the local maxima detected in a line, then $T_{k+1}$ would be used. This makes the algorithm suitable for images various respective contrasts. In our implementation, we use a three-level threshold, which is empirically determined based on high, medium and low level contrast of disc boundaries.

2.3.1.3. Preliminary Retina Structure Segmentation

Blood vessels, PPA and even optic cup may have strong boundaries which would typically be captured by the edge detection. When the edges from these structures form an ellipse stronger than the true optic disc, it often leads to an inaccurate ellipse detection. Thus, it is beneficial to remove (i.e. discard) the edges from these structures with minimal removal of edges from the disc boundary. A preliminary retina structure segmentation is employed by the enhanced disc segmentation module.

1) Preliminary Disc:

As the disc is normally the brightest part within the ROI, the preliminary disc segmentation is applied by comparing the ROI with a threshold $T_D$. $T_D$ is initialized to be the mean pixel value in the ROI. It is then increased until the proportion of pixels brighter than $T_D$ is no larger than 20%. The value 20% is empirically determined based on normal size of the optic disc compared with the total number of pixels within the ROI. The first mask is obtained as $Mask_1$=imdilate(D), where imdilate(•) denotes a morphological image dilation, D is a matrix with binary values and computed by:

$$D(x, y) = \begin{cases} 1 & I(x, y) > T_D \\ 0 & \text{otherwise} \end{cases} \quad (5)$$

The dilation is necessary as the boundary pixels of the disc often have relatively low pixel values. All edge pixels (x, y) with $Mask_1$(x, y)=0 are excluded.

2) Preliminary Cup:

The optic cup is the brightest part within the optic disc. Although it is difficult to find a general threshold to separate cup from disc, pixels with high intensity especially those close to 255 are most likely from the cup.

From this observation, a preliminary cup mask is empirically determined by $Mask_2$=imdilate(C), where C is computed by:

$$C(x, y) = \begin{cases} 1 & I(x, y) > T_C \\ 0 & \text{otherwise} \end{cases} \quad (6)$$

where $T_c$ is normally a value no less than 240. All edge pixels (x, y) with $Mask_2$(x, y)=1 are excluded.

3) Preliminary Blood Vessel:

The boundary of a blood vessel is normally stronger even than that of the disc. However, the pixel intensity across a blood vessel changes differently from that across the disc. In the disc, it increases while entering the disc and decreases while exiting. Across the blood vessels, it decreases first and increases again very soon. Thus, the blood vessel corresponds to one local minimum followed by one local maximum in the same row/column. We exclude every local minimum that is followed by a local maximum in the same row/column when detecting the descending edges. Similarly, we exclude every local maximum that follows a local minimum in the same row/column when detecting the ascending edges. The edge detection result from previous step in Section 2.3.2 is used. The enhanced disc segmentation module obtains another matrix V initialized to be all 1 s. Then, for each local maximum (x, y) from a row/column, its preceding $v_w$ pixels in that row/column in V are set to zero. For each local minimum (x, y) from a row/column, its subsequent $v_w$ pixels in that row/column in V are set to zero. Thus, if there is a local minimum before a local maximum, they are both set to zero. If the local maximum is before the local minimum, they would not be set to zero. $v_w$ is set to be slightly larger than normal vessel width. All edge pixels (x, y) with V (x, y)=0 are excluded.

4) Preliminary PPA: There are two types of PPAs, α-PPA and β-PPA. Since α-PPA is normally darker than disc, it is often excluded by the preliminary disc segmentation Mask1. However, β-PPA has a color similar to the disc and Mask1 does not exclude it. In such a scenario, the main difference between disc and PPA is that the former has a finer texture and the latter has a richer texture. One can design a preliminary PPA segmentation based on this. However, one challenge is that the texture is also rich at the superior and inferior of the disc where the blood vessels entering the disc. The PPA segmentation might be confused by the blood vessels. Another challenge is that PPA and disc share some edges as they are located beside each other. Thus, excluding PPA edges should not include those shared by the disc. Since the presence of PPA normally affects the disc segmentation by being included as part of disc, we propose to apply PPA segmentation later in the post-processing step in Section 2.3.5 below. So far, we have introduced the use of preliminary segmentation. This method presents basic algorithms for the preliminary segmentation. More sophisticated algorithms can be used.

Figure 18A:
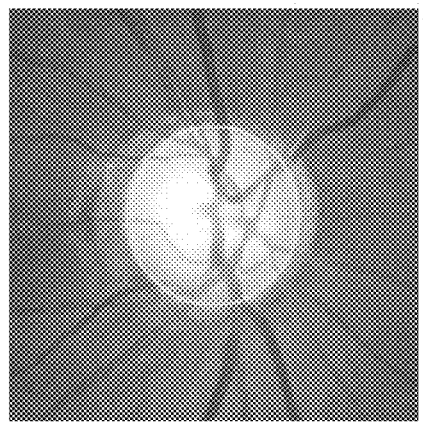
FIG. 18(a) shows a fundus image.
Figure 18B:
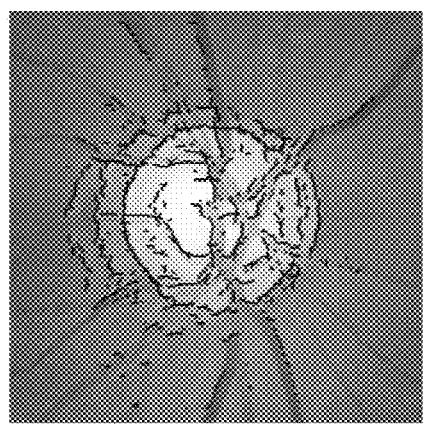
FIG. 18(b) shows edge points detected in the fundus image.
Figure 18C:
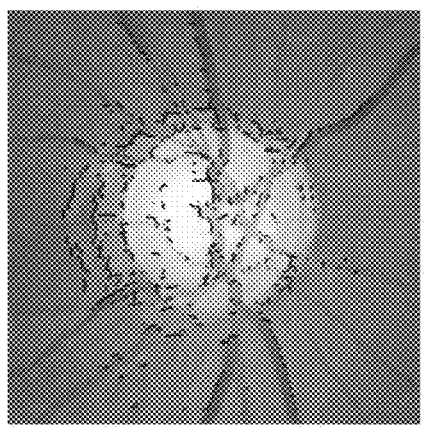
FIG. 18(c) shows edge points removed by a PRSS step of the process of FIG. 17.
Figure 18D:
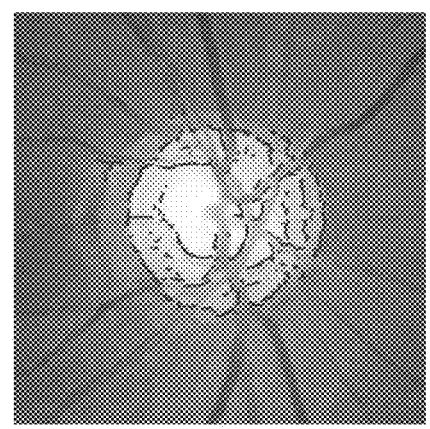
FIG. 18(d) shows the edge points remaining.
Figure 24:
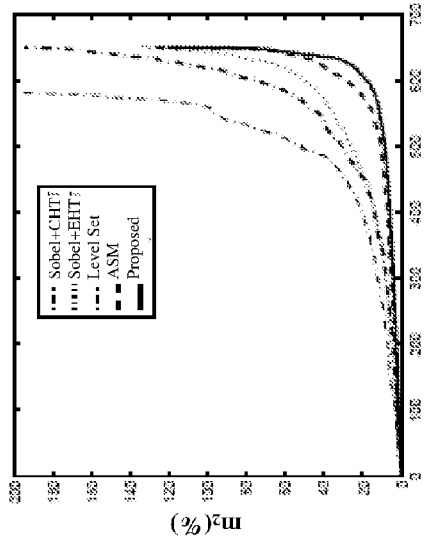
FIGS. 24(a), 24(b), and 24(c), numerically compare the output of the enhanced disc segmentation module of FIG. 17 to ground truth.
Figure 24:
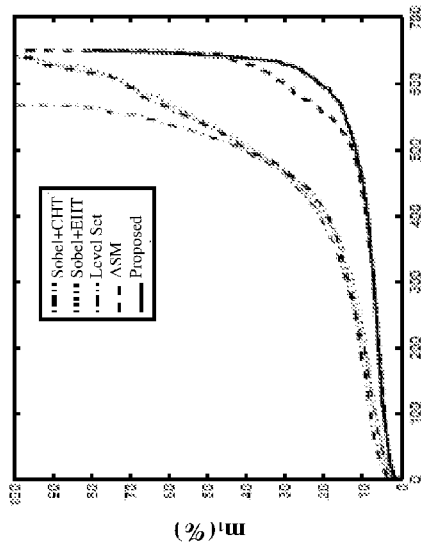

The edges after applying the preliminary segmentation would be used for disc segmentation in the next step. FIGS. 18(a), 18(b), 18(c), and 18(d) are examples to show how it helps. In FIG. 18(a), the ground truth of the optic disc is shown as a contour. In FIG. 18(b), all edges detected are shown superimposed on the fundus image. FIGS. 18(c) and (d) the lines superimposed on the fundus images indicate respectively the edges that are excluded by the mask and the edges that are kept. With the help of preliminary segmentation, only those edge points shown in FIG. 18(d) are used in the next step. The corresponding resultant segmented discs are shown in FIG. 24(b), which is described below.

2.3.1.4. Constrained Elliptical Hough Transform

An optic disc is approximately an ellipse. The parametric representation of an ellipse can be given by:

$$x(t) = xc + a \cos t \sin \phi - b \sin t \cos \phi$$

$$y(t) = yc + a \cos t \cos \phi - b \sin t \sin \phi \quad (7)$$

where the parameter t varies from 0 to $2\pi$, (xc, yc) is the center of the ellipse, a and b are the two radius values, and $\varphi$ is the rotation angle of the ellipse from the horizontal y-axis.

Figure 19:
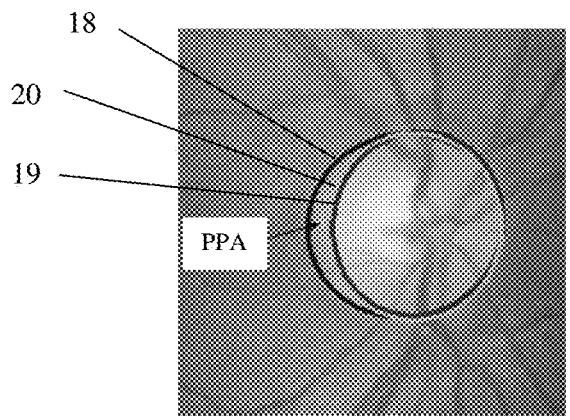
FIG. 19 compares fitting of the optic disc to an ellipse by the method of FIG. 17 with and without a constraint, in an image with mild PPA, and ground truth.

In most scenarios, the optic disc can be determined by the strongest ellipse within ROI. However, when PPA appears in ROI, it forms a stronger ellipse often, as shown in FIG. 19. Here the fundus image exhibits mild PPA. As PPA often appears in nasal and temporal sides of the disc, it forms an ellipse which is wider in the horizontal direction, i.e., a>b. However, most optic discs are wider in the vertical direction, a≤b. Thus, in our ellipse detection, we detect a second ellipse under the constraint of a/b≤γ (where γ can be 1 or slightly lower).

The algorithm for the constrained elliptical Hough transform is summarized as follows:
1) Set parameter (a, b, φ) for ellipse.
2) For each edge point (xe, ye), draw an ellipse centered at (xe, ye) with (a, b, φ) and increment all coordinates that the perimeter of the ellipse passes through in the accumulator A corresponding to the parameters.
3) Update (a, b, φ) and repeat step 2 for all (a, b, φ) from the parameter space.
4) Find the maximum value in A to get an ellipse centered at (x1, y1) and the corresponding ellipse parameters (a1, b1, φ1).
5) If a1/b1>γ, then find the maximum value in A subject to a/b≤γ to get a second ellipse centered at (x2, y2).
6) Determine the final ellipse. We use the second ellipse as the disc boundary if A(x2, y2)/A(x1, y1)>TA, otherwise, use the first ellipse. TA=0.9 is empirically selected.

The idea is that if a1/b1>γ, there is a higher chance that the first detected ellipse include some of PPA. Thus we would further check if there is another ellipse with a/b≤γ. If we find such an ellipse, then the second one is more likely to be the disc boundary. There are five unknown parameters xc, yc, a, b and φ. The problem of finding the ellipse is to search for the best fit in a 5D Hough space. Arbitrarily searching in the 5D space requires high computation. In order to reduce the computation as well as to improve the segmentation accuracy, following constraints are applied:
1) The ratio a/b is usually in a small range, typically between 0.8 and 1.2.
2) The value of a and b are within the range slightly broader than the range from the minimum to the maximum of the radius from the ground truth.

Besides reducing the computational load of the algorithm, these constraints also help excluding undesired ellipse shapes.

In FIG. 19, the line 18 illustrates the result of ellipse fitting without a constraint; line 19 illustrates the result of ellipse fitting with the constraint a/b≤γ; and line 20 illustrates ground truth.

2.3.1.5. PPA Detection

Figure 20:
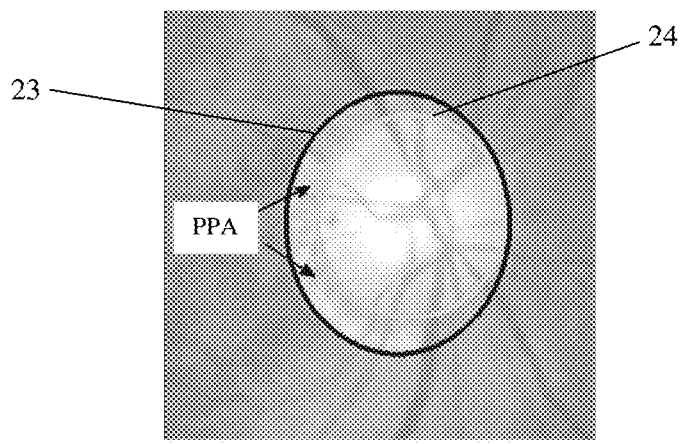
FIG. 20 compares fitting of the optic disc to an ellipse by the method of FIG. 17 in an image with moderate PPA, and ground truth.

Mistaking the PPA boundary for the disc boundary is one major cause of inaccuracy as some PPAs have a color similar to the optic disc. It happens when the PPA boundary forms an ellipse with part of disc boundary. FIG. 20 shows an example where the line 23 is the detected disc boundary, and line 24 is the ground truth. The PPAs are indicated by the arrows located beside the ground truth disc 24. However, they are included as part of the disc encircled by the detected line 23. Since these PPAs are located beside the detected ellipses, we propose to examine the area within each detected ellipse.

Figure 21:
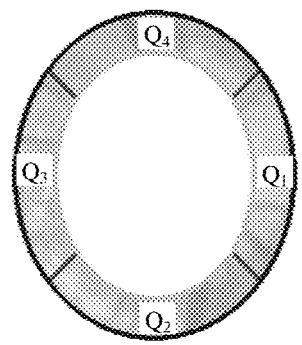
FIG. 21 illustrates a ring-shaped ROI used in the method of FIG. 17.

1) Region of Interest: A ring-shaped area, as shown in FIG. 21, is defined using the detected disc boundary, and used as the ROI which we further examine to evaluate the presence/absence of PPA. As the PPA often exists in one or several quadrants, the ROI ring is divided into several parts for examination. The enhanced disc segmentation module divides it into four quadrants (Q1, Q2, Q3 and Q4).

2) PPA Feature Extraction: In [11], entropy is used as a feature to tell the presence/absence of PPA. However, it relies on accurate disc segmentation to identify the region of interest and thus not applicable here. The entropy feature is not a good choice for segmentation as it responds positively not only to PPA, but also to vessels, disc boundary and etc. The enhanced disc segmentation module uses the following feature to determine the presence/absence of PPA.

The feature is extracted as follows. First, a smoothing process similar to the edge detection in section 2.2.2 is applied on the ROI I, except that we use a smaller J=10 and K=3 in the mean filter so that it would not smooth away the texture, changes in the PPA region. Then, new sets of local maxima and minima are detected. To be differentiable with the edge points in the edge detection step, we name them "feature points". Four matrices $F_h^{max}$, $F_h^{min}$, $F_v^{max}$ and $F_v^{min}$ are obtained, similar to the computation in equation (3) and (4).

A PPA region with rich texture usually contains more feature points than disc area. However, blood vessels also contribute to the feature points. Simply take all feature points as evidence of PPA texture may mistake blood vessels for PPA. To differentiate points from blood vessels, we make use of the fact that the length of the connected features points from PPA region are usually shorter than those from blood vessels.

3) Connectivity: A morphological processing Conn(F, p) is applied to remove from a binary matrix F all connected components that have fewer than p pixels. In this paper, we set p=15, determined experimentally to differentiate most blood vessels from PPA for a wide range of images. Moreover, the horizontal and vertical edges are processed separately:

$$CF_h^{max} = Conn(F_h^{max}, p)$$

$$CF_h^{min} = Conn(F_h^{min}, p)$$

$$CF_v^{max} = Conn(F_v^{max}, p)$$

$$CF_v^{min} = Conn(F_v^{min}, p) \qquad (8)$$

In each quadrant Qi, we count the number of horizontal and vertical feature points. When the amount of feature points exceeds a certain level, a PPA is considered as present that quadrant. Then the edge points near the detected disc boundary from the Qi would be removed. The elliptical Hough transform would be re-applied to get a new disc boundary.

2.3.1.6.

Figure 22:
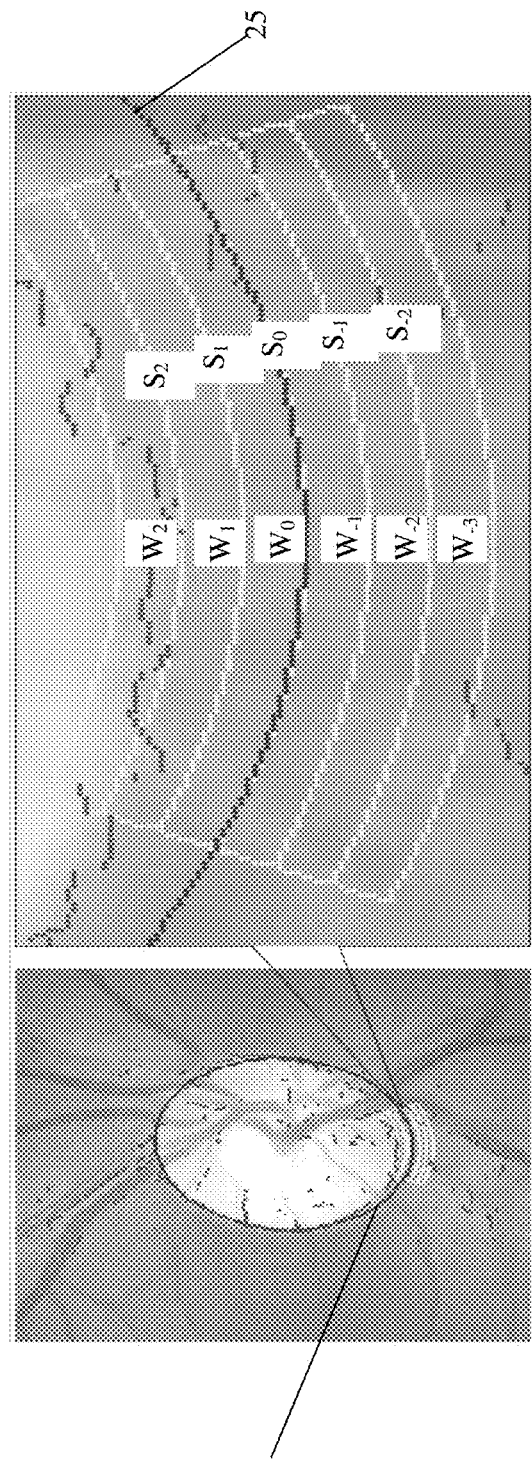
FIGS. 22(a) and 22(b) illustrate an ellipse correction search region used in the method of FIG. 17.

The ellipse fitting may over-fit the optic disc in some cases and result in the ellipse boundary lying away from the true disc boundary in some areas. FIG. 22(a) is an example where the line 25 is the detected ellipse. On the superior side, there are very few edge points around the detected ellipse, which indicates an inaccurate disc boundary in this area. An ellipse boundary correction is necessary to further improve the disc boundary accuracy. In the boundary correction, we search on both sides of the current detected disc boundary in quadrant Qi, i=1, 2, 3, 4. The search region is the center half portion from each quadrant and divided into several small windows, as shown in FIG. 22(b) for Q2. FIG. 22(b) is an enlarged portion of FIG. 22(a). When the number of edge points in $S_0$ is below certain level, the enhanced disc segmentation module searches in the neighbourhood $S_0$ for the nearest window with more edge points. It adjusts the ellipse parameters such that the new disc boundary passes the new window.

2.3.2 Experimental Results 2.3.2.1. ORIGA Light Database

We use the ORIGA light [9] database which contains 650 images including 168 from glaucoma eyes and 482 from normal eyes for the testing. The boundaries of the optic disc and the cup have been manually marked by trained professionals from Singapore Eye Research Institute using ORIGA-GT on desktop machines. Below we compare the disc boundary identified by the enhanced disc segmentation module, and compare it with the ground truth.

2.3.2.2. Evaluation Metrics

Several metrics have been commonly used to evaluate the accuracy of the segmentation.

$$m_1 = \left(1 - \frac{OD_{seg} \cap OD_{ref}}{OD_{seg} \cup OD_{ref}}\right) \times 100\% \qquad (9)$$

$$m_2 = \frac{|OD_{seg} - OD_{ref}|}{OD_{ref}} \times 100\% \qquad (10)$$

where $OD_{seg}$ and $OD_{ref}$ denote the segmented disc and the ground truth disc respectively. In addition, as the vertical disc diameter is used in the cup to disc ratio computation, we also look at the accuracy of the vertical disc diameter.

$$m_{VD} = \frac{|VD_{seg} - VD_{ref}|}{VD_{ref}} \times 100\% \qquad (11)$$

where $VD_{seg}$ and $VD_{ref}$ represent the vertical diameter of the segmented disc and ground truth disc respectively. A lower score indicates a better performance with 0 indicates perfect segmentation.

2.3.2.3. Results

Figure 23:
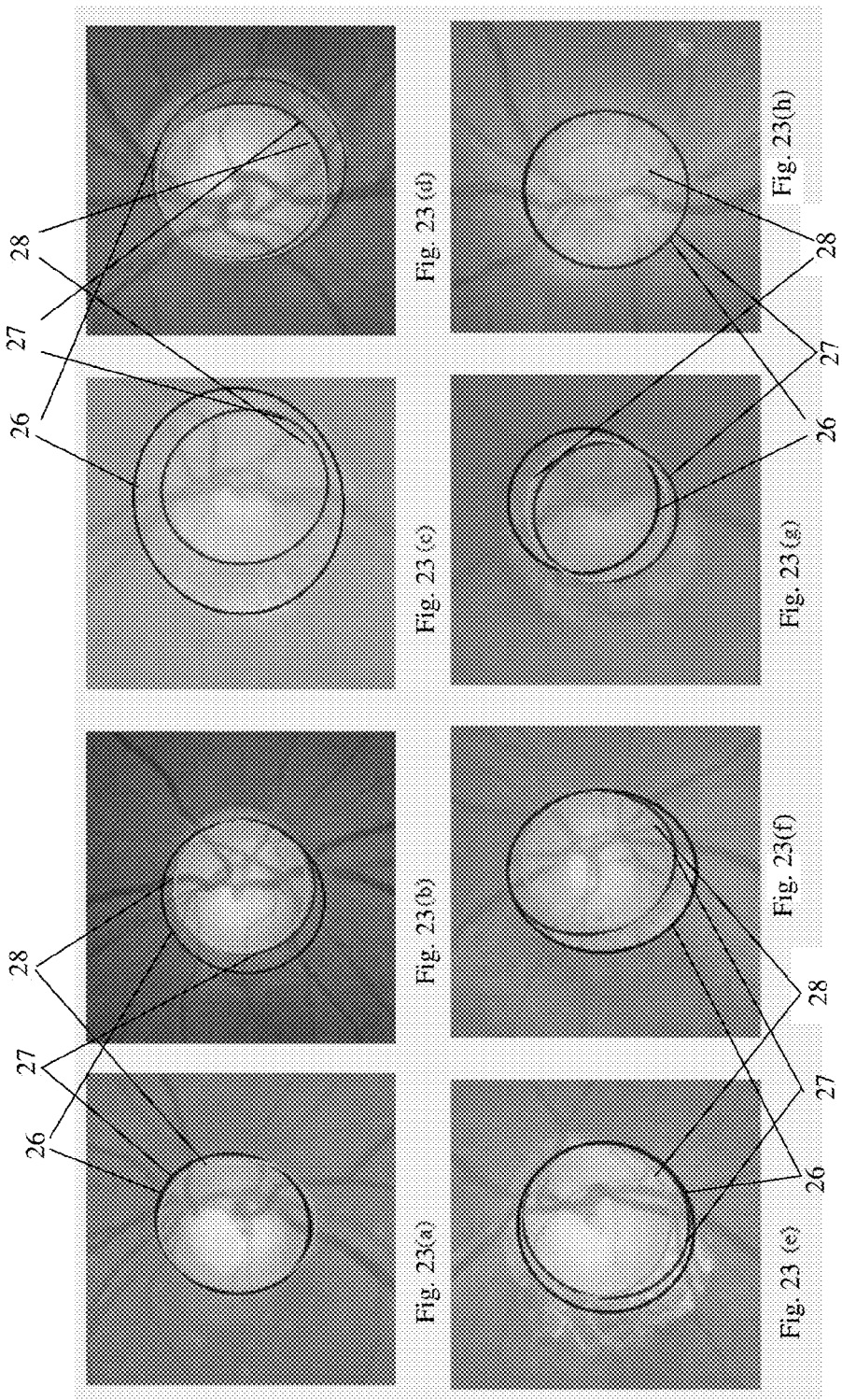
FIGS. 23(a), 23(b), 23(c), 23(d), 23(e), 23(f), 23(g), and 23(h), show sample results produced by the enhanced disc segmentation module of FIG. 17.

We perform the tests by the proposed method and compare with other methods. FIGS. 23(a), 23(b), 23(c), 23(d), 23(e), 23(f), 23(g), and 23(h) show several examples of the segmentation results compared with the ground truth. Here, we highlight the benefit of using preliminary segmentation. In FIGS. 23(a), 23(b), 23(c), 23(d), 23(e), 23(f), 23(g), and 23(h), the lines 26 are the detected disc based on all edge points without using PRSS, the lines 27 are the results with PRSS, and the lines 28 are the ground truth. It will be seen that divergence of the line 27 from the line 28 is consistently less than the divergence of the line 26 from the line 28. For images without PPA, both the results 26, 27 are close to the ground truth, as shown in FIG. 23(a). For images with PPAs as shown in FIG. 23(b)-FIG. 23(g), the method without preliminary segmentation is often trapped by the PPA boundary while the proposed method finds the disc boundary more accurately. FIG. 23(h) is an example in which both methods fail to find the disc boundary accurately due to non-obvious disc boundary. This is one of the reasons which may lead to inaccurate segmentation by the proposed method. Next, we show the improvements which may be achieved by post-processing.

We also compare our method with other methods. The first method uses Sobel edge detection combined with circular Hough transform as in [7]. In the second method, we replace circular Hough transform with elliptical Hough transform to see the benefit of elliptical Hough transform. Ellipse Hough transform improves the performance slightly, however, both methods often trapped by PPA, similar to the case without PRSS in FIG. 23. The third and fourth are level-set approach [6] and the active shape model (ASM) based approach [10]. The level set approach does not perform well for cases with strong PPA boundary or weak disc boundary. The ASM approach produces similar results compared with the proposed method, except for some cases with large segmentation due to poor initialization.

Table 2 shows the average values of the evaluation metrics $m_1$, $m_2$ and $m_{VD}$ based on the performance of the 650 images. Table 3 shows the distribution of the segmentation results for both ASM and the proposed method. ASM method provides more results with $m_1$ no more than 5%, however, it also provides more results with $m_1$ larger than 25%.

TABLE 2

MEAN VALUE OF THE METRICS FROM 650 IMAGES BY VARIOUS SEGMENTATION METHODS

| Method | $m_1$ | $m_2$ | $m_{VD}$ |
|---|---|---|---|
| Sobel + CHT | 26.1% | 22.8% | 11.2% |
| Sobel + EHT | 25.2% | 17.7% | 8.7% |
| Level Set | 23.1% | 29.9% | 15.6% |
| ASM | 11.3% | 9.7% | 5.5% |
| Proposed | 10.0% | 7.4% | 4.9% |

TABLE 3

DISTRIBUTION OF THE RESULTS BY THE PROPOSED METHOD

| Method | ASM | | | Proposed | | |
|---|---|---|---|---|---|---|
| Measurement | $m_1$ | $m_2$ | $m_{VD}$ | $m_1$ | $m_2$ | $m_{VD}$ |
| >25% | 75 | 58 | 20 | 34 | 28 | 12 |
| 20%-25% | 20 | 16 | 15 | 21 | 16 | 7 |
| 15%-20% | 31 | 25 | 11 | 38 | 20 | 10 |
| 10%-15% | 97 | 68 | 44 | 106 | 56 | 44 |
| 5%-10% | 284 | 190 | 124 | 333 | 182 | 135 |
| ≤5% | 143 | 293 | 436 | 118 | 348 | 442 |
| Total | 650 | 650 | 650 | 650 | 650 | 650 |

Figure 24C:
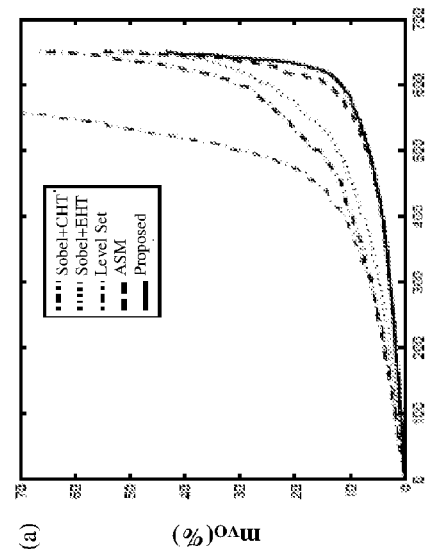

FIGS. 24(a), 24(b) and 24(c) show respectively the values of $m_1$, $m_2$ and $m_{VD}$ for 650 images by different methods sorted from minimum to maximum. A lower score indicates a better performance with 0 for perfect segmentation. As shown in by the testing results based on 650 images, the enhanced disc segmentation module is more accurate, as shown in FIGS. 24(a), 24(b), and 24(c) by the fact that its result (indicted by the solid lines) is always the lowest.

2.4 GAIA Module

Figure 25:
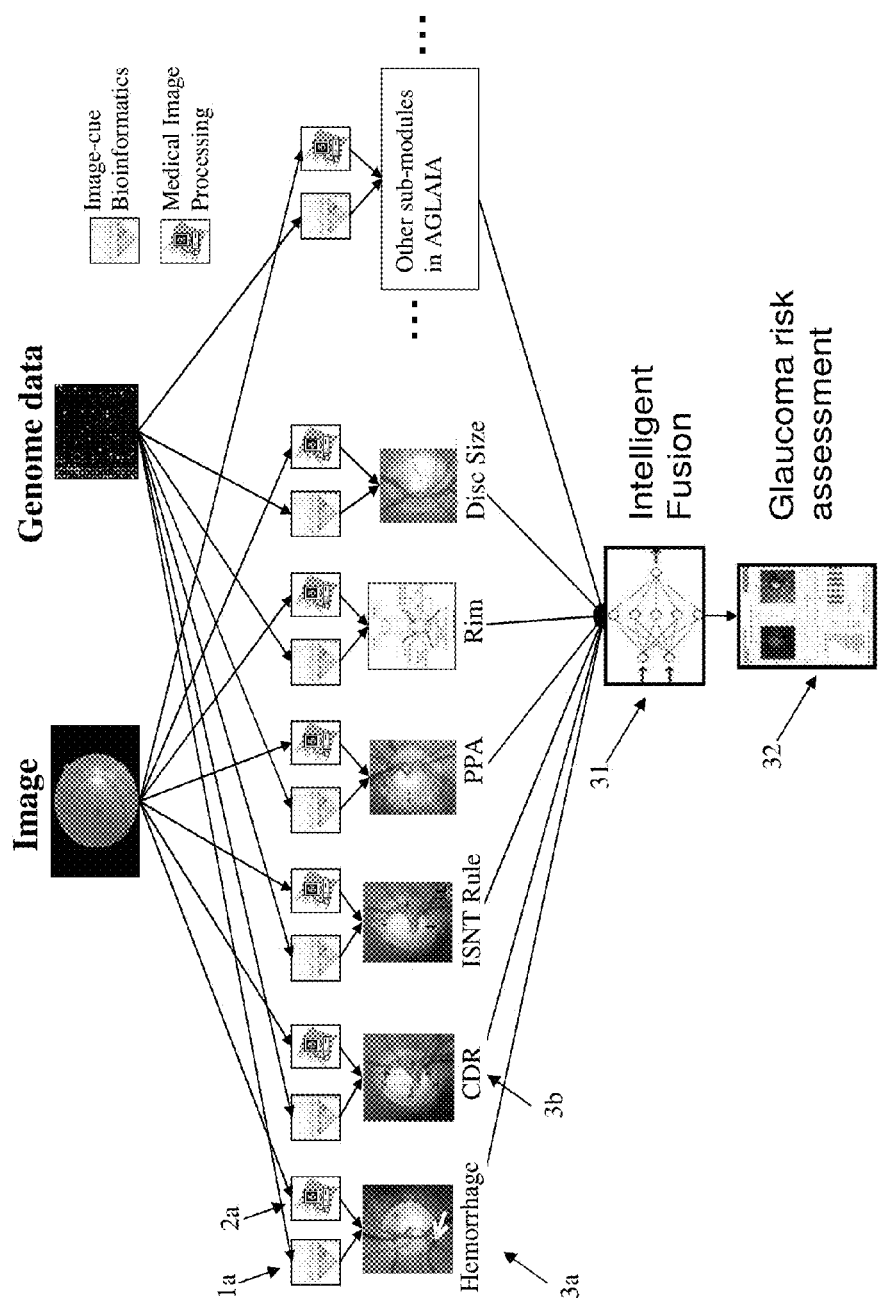
FIG. 25 illustrates a further function of a toolbox unit of the structure of FIG. 7.

As noted above, the toolbox 9 of FIG. 7 may implement an interaction between the unit 4 and GWAS module 6. FIG. 25 illustrates the consequent flow of information.

Figure 7:
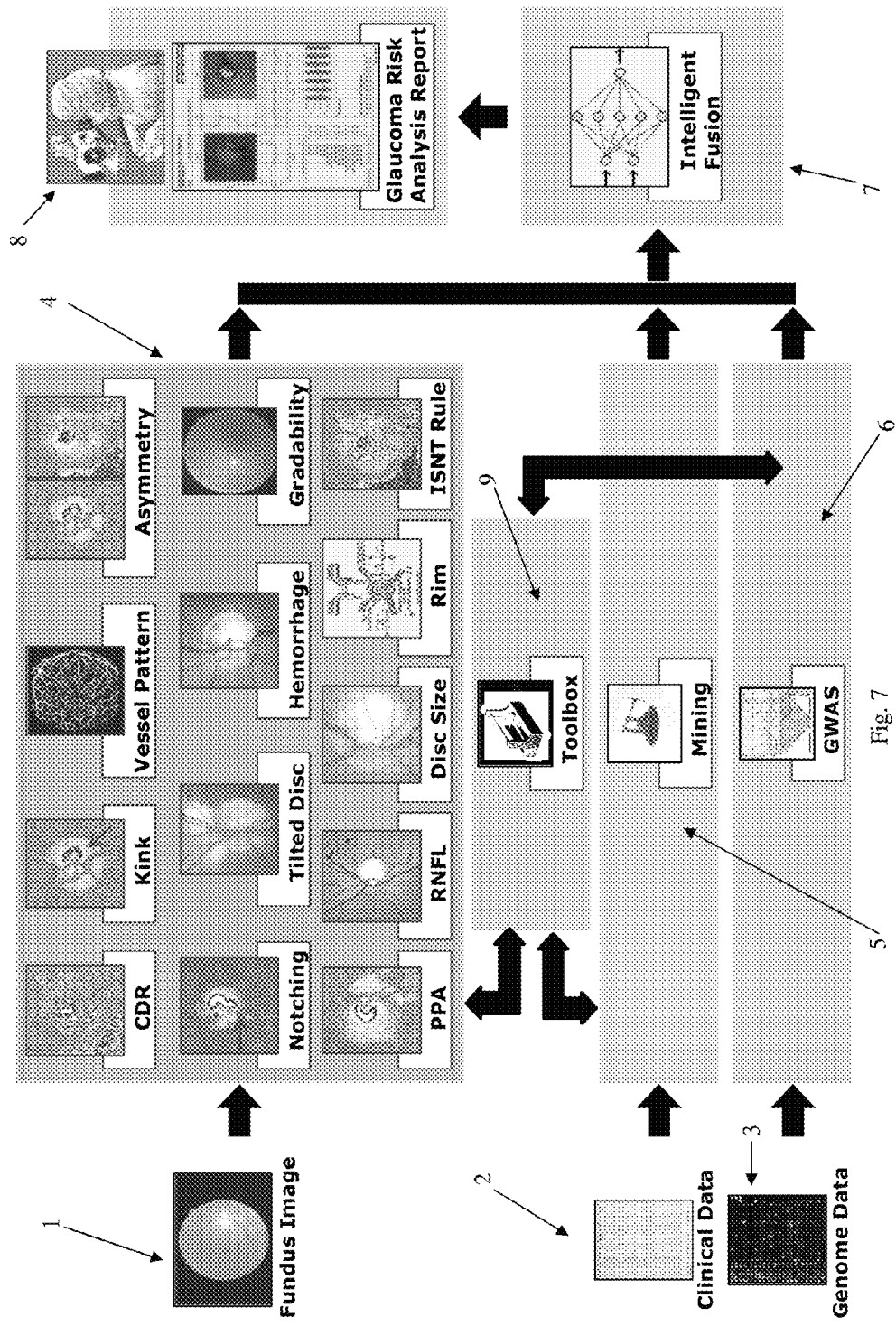
FIG. 7 shows an alternative way of denoting the structure of the embodiment of FIG. 2, to explain four optional features of the embodiment.

Again, the inputs are the fundus images 1 and the genome data 3 (the medical data 2 is omitted from the diagram for simplicity, though if it is available it is handled in the same way as in FIG. 7).

We denote the number of indicators obtained by the unit 4 by m. Each of the m indicators is obtained from a respective adaptive model module 3a, ..., 3m. The adaptive model modules 3a, ..., 3m each have two input modules 1a, ..., 1m and 2a, ..., 2m respectively. For simplicity only a few of these reference numerals are shown in FIG. 4. The input modules 1a-1m receive the genome data 3, and extract from it genetic data relevant to the modules 3a-3m. The input modules 2a-2m receive the image data, and perform medical image processing. Thus, the adaptive model modules 3a-3m receive the results of both image and GWAS analysis, in order to produce their respective indicator of glaucoma.

A second adaptive model unit 31 receives the outputs of the first adaptive model modules 3a-3m, and performs an intelligent fusion of the results, to form a glaucoma risk assessment 32. By performing this function, the toolbox 9 combines GWAS and medical image analysis, benefitting from the multiple analysis, the performance can be boosted. Thus, the adaptive model is a two-stage process.

REFERENCES

The disclosure in the following references is hereby incorporated in its entirety:

[1]. 1. Wishal D. Ramdas, Leonieke M. E. van Koolwijk, M. Kamran lkram, Nomodo M. Jansonius, Paulus T. V. M. De Jong, Arthur A. B. Bergen, Aaron Isaacs, Najaf Amin, Yurii S. Aulchenko, Roger C. W. Wolfs, Albert Hofman, Fernando Rivadeneira, Ben A. Oostra, Andre G. Uitterlinden, Pirro Hysi, Christopher J. Hammond, Hans G. Lemij, Johannes R. Vingerling, Caroline C. W. Klaver, Cornelia M. Van Buijn, "A Genome-Wide Association Study of Optic Disc Parameters", PLoS Genetics, June 2010.

[2]. J. Liu, D. W. K. Wong, J. H. Lim, H. Li, N. M. Tan, Z. Zhang, T. Y Wong, R. Lavanya, "ARGALI: An Automatic Cup-To-Disc Ratio Measurement System For Glaucoma Analysis Using Level-Set Image Processing", 13th International Conference on Biomedical Engineering (ICBME2008), December 2008.

[3]. J. Liu, D. W. K. Wong, J. H. Lim, X. Jia, F. Yin, H. Li, W. Xiong, T. Y. Wong, "Optic cup and disc extraction from retinal fundus images for determination of cup-to-disc ratio," Conf Proc IEEE ICIEA, 1828-1832, 2008.

[4]. D. W. K. Wong, J. Liu, J. H. Lim., H. Li, X. Jia, F. Yin, T. Y. Wong, "Automated detection of kinks from blood vessels for optic cup segmentation in retinal images", accepted for SPIE Medical Imaging 2009, February 2009.

[5]. N. Inoue, K. Yanashima, K. Magatani, and T. A. K. T. Kurihara, "Development of a simple diagnostic method for the glaucoma using ocular Fundus pictures," 27th Annual International Conference of the, Engineering in Medicine and Biology Society, 2005.

[6]. M. D. Abramoff, W. L. M. Alward, E. C. Greenlee, L. Shuba, C. Y. Kim, J. H. Fingert, and Y. H. Kwon, "Automated Segmentation of the Optic Disc from Stereo Color Photographs Using Physiologically Plausible Features," Investigative Ophthalmology and Visual Science, vol. 48, pp. 1665, 2007.

[7]. J. Xu, O. Chutatape, E. Sung, C. Zheng, and P. Chew Tec Kuan, "Optic disc feature extraction via modified deformable model technique for glaucoma analysis," Pattern Recognition, vol. 40, pp. 2063-2076, 2007.

[8] X. Zhu and R. M. Rangayyan, "Detection of the optic disc in images of the retina using the hough transform," in International Conference of the IEEE Engineering in Medicine and Biology Society, 2008, pp. 3546-3549.

[9] Z. Zhang, F. Yin, W. K. Wong J. Liu, N. M. Tan, B. H. Lee, J. Cheng, and T. Y. Wong, "Origa-light: An online retinal fundus image database for glaucoma analysis and research," in International Conference of the IEEE Engineering in Medicine and Biology Society, 2010.

[10] Z. Zhang, B. H. Lee, J. Liu, D. W. K. Wong, N. M. TAN, J. H. Lim, F. S. Yin, W. M. Huang, and H. Li, "Optic disc region of interest localization in fundus image for glaucoma detection in argali," in Proc. of the 5th International Conference on Industrial Electronics & Applications, 2010.

[11] J. Liu, D. W. K. Wong, J. H. Lim, N. M. Tan, Z. Zhang, H. Li, F. Yin, B. H. Lee, S. M. Saw, L. Tong, and T. Y. Wong, "Detection of pathological myopia by pamela with texture-based features through an svm approach," Journal of Healthcare Engineering, vol. 1, no. 1, pp. 1-11, 2010.

What is claimed is:

1. A method of processing a non-stereo fundus image to identify whether a plurality of glaucoma indicators are present, the method comprising:
performing a texture analysis by extracting numerical parameters from the fundus image;
determining whether the numerical parameters meet a quality criterion; and
only if the determination indicates that the numerical parameters meet the quality criterion, analyzing the fundus image by a plurality of image processing algorithms to determine whether the glaucoma indicators are present.

2. The method according to claim 1 wherein the texture analysis comprises at least one of: (i) a wavelet decomposition; or (ii) measuring the degree to which the image contains a plurality of predetermined image features.

3. The method according to claim 1 in which the determining is performed using an adaptive model trained to perform the determination using training data comprising (i) images which are known to either meet or not meet a quality criterion, and (ii) the corresponding numerical parameters.

4. The method according to claim 1, further comprising before performing the texture analysis, converting the fundus image into a predefined format if the image is not already in that format.

5. The method according to claim 1 further comprising extracting further numerical parameters from the fundus image, said further numerical parameters being used as control parameters in one or more of the image processing algorithms.

6. A computer system comprising:
a memory to store a non-stereo fundus image; and
a processor arranged to process the non-stereo fundus image to identify whether a plurality of glaucoma indicators are present, the processor to:
perform a texture analysis by extracting numerical parameters from the fundus image,
determine whether the numerical parameters meet a quality criterion, and
only if the determination indicates that the numerical parameters meet the quality criterion, analyze the fundus image by a plurality of image processing algorithms to determine whether the glaucoma indicators are present.

7. A non transitory computer readable storage medium storing instructions, which when executed by a processor of a computer system, cause the processor to perform a method, comprising:
performing a texture analysis by extracting numerical parameters from a fundus image,
determining whether the numerical parameters meet a quality criterion, and
only if the determination indicates that the numerical parameters meet the quality criterion, analyzing the fundus image by a plurality of image processing algorithms to determine whether the glaucoma indicators are present.

* * * * *